US012624389B2

(12) United States Patent
Lindsay et al.

(10) Patent No.: US 12,624,389 B2
(45) Date of Patent: May 12, 2026

(54) METHODS FOR SEQUENCING BIOPOLYMERS

(71) Applicant: ARIZONA BOARD OF REGENTS ON BEHALF OF ARIZONA STATE UNIVERSITY, Scottsdale, AZ (US)

(72) Inventors: Stuart Lindsay, Phoenix, AZ (US); Eathen Ryan, Tempe, AZ (US); Bintian Zhang, Tempe, AZ (US); Xu Wang, Tempe, AZ (US)

(73) Assignee: ARIZONA BOARD OF REGENTS ON BEHALF OF ARIZONA STATE UNIVERSITY, Scottsdale, AZ (US)

( * ) Notice: Subject to any disclaimer, the term of this patent is extended or adjusted under 35 U.S.C. 154(b) by 1001 days.

(21) Appl. No.: 17/832,316

(22) Filed: Jun. 3, 2022

(65) Prior Publication Data

US 2022/0389502 A1 Dec. 8, 2022

Related U.S. Application Data

(60) Provisional application No. 63/197,901, filed on Jun. 7, 2021.

(51) Int. Cl.
C12Q 1/6869 (2018.01)
C12Q 1/00 (2006.01)
G01N 27/12 (2006.01)

(52) U.S. Cl.
CPC ........... C12Q 1/6869 (2013.01); C12Q 1/005 (2013.01); G01N 27/12 (2013.01)

(58) Field of Classification Search
None
See application file for complete search history.

(56) References Cited

U.S. PATENT DOCUMENTS

| | | | |
|---|---|---|---|
| 5,198,543 | A | 3/1993 | Blanco |
| 6,022,688 | A | 2/2000 | Jurinke et al. |
| 6,391,558 | B1 | 5/2002 | Henkens et al. |
| 6,758,961 | B1 | 7/2004 | Vogel et al. |

(Continued)

FOREIGN PATENT DOCUMENTS

| | | |
|---|---|---|
| CN | 1325490 A | 12/2001 |
| CN | 1916630 A | 2/2007 |

(Continued)

OTHER PUBLICATIONS

Kang Y., et al., "DC-Dielectrophoretic Separation of Biological Cells by Size", Biomedical Microdevices, vol. 10, pp. 243-249, 2008, pp. 243-249.

(Continued)

*Primary Examiner* — Jennifer Wecker
*Assistant Examiner* — Jonathan Bortoli
(74) *Attorney, Agent, or Firm* — Casimir Jones, S.C.; Peter J. Schlueter

(57) ABSTRACT

The present disclosure provides devices, systems, and methods related to sequencing a biopolymer. In particular, the present disclosure relates to methods for sequencing a polynucleotide using a bioelectronic device that includes protein assemblies used as coupling molecules in bioelectronic circuits. The present disclosure also provides multimeric protein assemblies with various combinations of live and dead subunits arranged to maximize conduction.

16 Claims, 8 Drawing Sheets

(56) References Cited

U.S. PATENT DOCUMENTS

| | | | |
|---|---|---|---|
| 6,824,974 B2 | 11/2004 | Pisharody et al. |
| 7,632,671 B2 | 12/2009 | Tong |
| 7,785,785 B2 | 8/2010 | Pourmand et al. |
| 8,628,649 B2 | 1/2014 | Lindsay et al. |
| 8,753,893 B2 | 6/2014 | Liu et al. |
| 8,961,757 B2 | 2/2015 | Nuckolls et al. |
| 8,968,540 B2 | 3/2015 | Reinhart et al. |
| 9,140,682 B2 | 9/2015 | Lindsay et al. |
| 9,274,430 B2 | 3/2016 | Gyarfas et al. |
| 9,376,713 B2 | 6/2016 | Bashir et al. |
| 9,395,352 B2 | 7/2016 | Lindsay et al. |
| 9,593,372 B2 | 3/2017 | Lindsay et al. |
| 9,766,248 B2 | 9/2017 | Lindsay et al. |
| 9,810,681 B2 | 11/2017 | Lindsay et al. |
| 9,938,586 B2 | 4/2018 | Liang et al. |
| 10,036,064 B2 | 7/2018 | Merriman et al. |
| 10,047,392 B2 | 8/2018 | Ivankin et al. |
| 10,051,722 B2 | 8/2018 | Yamamoto et al. |
| 10,227,694 B2 | 3/2019 | Jin et al. |
| 10,378,103 B2 | 8/2019 | Jin et al. |
| 10,379,102 B2 | 8/2019 | Lindsay et al. |
| 10,422,787 B2 | 9/2019 | Lindsay et al. |
| 10,508,296 B2 | 12/2019 | Merriman et al. |
| 10,526,696 B2 | 1/2020 | Jin et al. |
| 10,584,410 B2 | 3/2020 | Jin et al. |
| 10,597,767 B2 | 3/2020 | Merriman et al. |
| 10,648,941 B2 | 5/2020 | Merriman et al. |
| 10,712,334 B2 | 7/2020 | Choi et al. |
| 10,737,263 B2 | 8/2020 | Choi et al. |
| 10,913,966 B2 | 2/2021 | Merriman et al. |
| 11,630,098 B2 | 4/2023 | Lindsay et al. |
| 11,808,755 B2 | 11/2023 | Lindsay et al. |
| 11,959,905 B2 | 4/2024 | Lindsay et al. |
| 2003/0064390 A1 | 4/2003 | Schuelein et al. |
| 2003/0098248 A1 | 5/2003 | Vogel et al. |
| 2003/0124572 A1 | 7/2003 | Umek et al. |
| 2004/0146863 A1 | 7/2004 | Pisharody et al. |
| 2004/0249124 A1 | 12/2004 | Caruso et al. |
| 2005/0074871 A1 | 4/2005 | Albert et al. |
| 2005/0266456 A1 | 12/2005 | Williams et al. |
| 2005/0285275 A1 | 12/2005 | Son et al. |
| 2006/0154489 A1 | 7/2006 | Tornow et al. |
| 2008/0218184 A1 | 9/2008 | White et al. |
| 2009/0017571 A1 | 1/2009 | Nuckolls et al. |
| 2009/0215156 A1 | 8/2009 | Chung et al. |
| 2009/0226899 A1 | 9/2009 | Chen |
| 2009/0295372 A1 | 12/2009 | Krstic et al. |
| 2010/0084276 A1 | 4/2010 | Lindsay |
| 2010/0184062 A1 | 7/2010 | Steinmuller-Nethl et al. |
| 2010/0206731 A1 | 8/2010 | Lau et al. |
| 2010/0285514 A1 | 11/2010 | Claussen et al. |
| 2011/0098218 A1 | 4/2011 | Han et al. |
| 2011/0166034 A1 | 7/2011 | Kwong et al. |
| 2011/0312529 A1 | 12/2011 | He et al. |
| 2012/0228386 A1 | 9/2012 | Wu et al. |
| 2012/0231447 A1 | 9/2012 | Zhang et al. |
| 2012/0258870 A1 | 10/2012 | Schwartz et al. |
| 2012/0288948 A1 | 11/2012 | Lindsay et al. |
| 2013/0109577 A1 | 5/2013 | Korlach et al. |
| 2013/0302901 A1 | 11/2013 | Lindsay et al. |
| 2014/0141525 A1 | 5/2014 | Albert et al. |
| 2014/0231274 A1 | 8/2014 | Oki et al. |
| 2015/0010935 A1 | 1/2015 | Lindsay et al. |
| 2015/0017655 A1 | 1/2015 | Huang et al. |
| 2015/0086994 A1 | 3/2015 | Williams et al. |
| 2015/0142327 A1 | 5/2015 | Ashcroft et al. |
| 2015/0144506 A1 | 5/2015 | Lindsay et al. |
| 2015/0285818 A1 | 10/2015 | Banala et al. |
| 2015/0362459 A1 | 12/2015 | Chung et al. |
| 2016/0018384 A1 | 1/2016 | Lindsay et al. |
| 2016/0025702 A1 | 1/2016 | Lindsay et al. |
| 2016/0082739 A1 | 3/2016 | Takagiwa |
| 2016/0083789 A1 | 3/2016 | Turner et al. |
| 2016/0097759 A1 | 4/2016 | Lindsay et al. |
| 2016/0108002 A1 | 4/2016 | Zhang et al. |

| | | | |
|---|---|---|---|
| 2016/0146828 A1 | 5/2016 | Lindsay et al. |
| 2016/0177383 A1 | 6/2016 | Ashcroft et al. |
| 2016/0194698 A1 | 7/2016 | Lindsay |
| 2016/0258925 A1 | 9/2016 | Gyarfas et al. |
| 2016/0280723 A1 | 9/2016 | Zhang et al. |
| 2016/0282295 A1 | 9/2016 | Wang et al. |
| 2016/0319343 A1 | 11/2016 | Korlach et al. |
| 2017/0003245 A1 | 1/2017 | Lindsay et al. |
| 2017/0016852 A1 | 1/2017 | Lindsay et al. |
| 2017/0037462 A1 | 2/2017 | Turner et al. |
| 2017/0038333 A1 | 2/2017 | Turner et al. |
| 2017/0038369 A1 | 2/2017 | Lindsay et al. |
| 2017/0044605 A1 | 2/2017 | Merriman et al. |
| 2017/0067902 A1 | 3/2017 | Zhang et al. |
| 2017/0121761 A1 | 5/2017 | Eichen et al. |
| 2017/0137389 A1 | 5/2017 | Zhang et al. |
| 2017/0168039 A1 | 6/2017 | Lindsay et al. |
| 2017/0204066 A1 | 7/2017 | Lindsay et al. |
| 2017/0276678 A1 | 9/2017 | Ervin et al. |
| 2017/0343558 A1 | 11/2017 | Lindsay et al. |
| 2018/0031549 A1 | 2/2018 | Chen et al. |
| 2018/0051332 A9 | 2/2018 | Esfandyarpour et al. |
| 2018/0073071 A1 | 3/2018 | Ju et al. |
| 2018/0095081 A1 | 4/2018 | Albert et al. |
| 2018/0120286 A1 | 5/2018 | Lindsay et al. |
| 2018/0155773 A1 | 6/2018 | Gunderson et al. |
| 2018/0180567 A1 | 6/2018 | Li et al. |
| 2018/0305727 A1 | 10/2018 | Merriman et al. |
| 2018/0340220 A1 | 11/2018 | Merriman et al. |
| 2019/0004003 A1 | 1/2019 | Merriman et al. |
| 2019/0041355 A1 | 2/2019 | Merriman et al. |
| 2019/0094175 A1 | 3/2019 | Merriman et al. |
| 2019/0112643 A1 | 4/2019 | Aran et al. |
| 2019/0234902 A1 | 8/2019 | Lima, Jr. et al. |
| 2019/0309008 A1 | 10/2019 | Ju et al. |
| 2019/0317040 A1 | 10/2019 | Lindsay et al. |
| 2019/0330695 A1 | 10/2019 | Guo et al. |
| 2019/0376135 A1 | 12/2019 | Mandell et al. |
| 2020/0157595 A1 | 5/2020 | Merriman et al. |
| 2021/0114025 A1 | 4/2021 | De et al. |
| 2021/0208127 A1 | 7/2021 | Lindsay et al. |
| 2021/0269869 A1 | 9/2021 | Lindsay |
| 2021/0325379 A1 | 10/2021 | Lindsay et al. |
| 2021/0340614 A1* | 11/2021 | Lindsay ............... C12Q 1/6869 |
| 2021/0372986 A1 | 12/2021 | Lindsay |
| 2022/0098635 A1 | 3/2022 | Lindsay et al. |
| 2022/0196646 A1 | 6/2022 | Lindsay et al. |
| 2022/0252542 A1 | 8/2022 | Merriman et al. |
| 2022/0316002 A1 | 10/2022 | Lindsay et al. |
| 2023/0243807 A1 | 8/2023 | Lindsay et al. |

FOREIGN PATENT DOCUMENTS

| | | | |
|---|---|---|---|
| CN | 101365827 A | 2/2009 |
| CN | 101400800 A | 4/2009 |
| CN | 102414560 A | 4/2012 |
| CN | 104105797 A | 10/2014 |
| CN | 104359946 | 2/2015 |
| CN | 104955958 A | 9/2015 |
| CN | 105283560 A | 1/2016 |
| CN | 105378113 A | 3/2016 |
| CN | 107082792 A | 8/2017 |
| CN | 107666962 A | 2/2018 |
| CN | 107683337 A | 2/2018 |
| CN | 108018270 A | 5/2018 |
| CN | 109154024 A | 1/2019 |
| CN | 109891233 A | 6/2019 |
| EP | 3976814 A1 | 4/2022 |
| JP | H01248570 A | 10/1989 |
| JP | H0719927 B2 | 3/1995 |
| JP | 2012021972 A | 2/2012 |
| JP | 2016188794 A | 11/2016 |
| JP | 2018500905 A | 1/2018 |
| TW | 201409690 A | 3/2014 |
| WO | WO-9931503 A1 | 6/1999 |
| WO | WO-2012050533 A1 | 4/2012 |
| WO | WO 2013/038272 | 3/2013 |
| WO | WO-2013154999 A2 | 10/2013 |
| WO | WO 2014/074727 | 5/2014 |

(56) References Cited

FOREIGN PATENT DOCUMENTS

| WO | WO 2015/130781 | 9/2015 | | |
| WO | WO 2015/131073 | 9/2015 | | |
| WO | WO 2015/161119 | 10/2015 | | |
| WO | WO-2015170784 A1 | 11/2015 | | |
| WO | WO-2016100635 A1 | 6/2016 | | |
| WO | WO 2016/161402 | 10/2016 | | |
| WO | WO 2016/210386 | 12/2016 | | |
| WO | WO-2017042038 A1 | 3/2017 | | |
| WO | WO 2017/084998 | 5/2017 | | |
| WO | WO 2017/123416 | 7/2017 | | |
| WO | WO-2017132567 A1 | 8/2017 | | |
| WO | WO-2017132586 A1 | 8/2017 | | |
| WO | WO-2017148861 A1 | 9/2017 | | |
| WO | WO 2017/189930 | 11/2017 | | |
| WO | WO 2018/026855 | 2/2018 | | |
| WO | WO-2018098286 A1 | 5/2018 | | |
| WO | WO-2018132457 A1 | 7/2018 | | |
| WO | WO-2018200687 A1 | 11/2018 | | |
| WO | WO-2018208505 A1 | 11/2018 | | |
| WO | WO-2019046589 A1 | 3/2019 | | |
| WO | WO 2019/086305 | 5/2019 | | |
| WO | WO-2019161381 A1 | 8/2019 | | |
| WO | WO 2019/211622 | 11/2019 | | |
| WO | WO 2019/222527 | 11/2019 | | |
| WO | WO-2019217600 A1 | 11/2019 | | |
| WO | WO 2020/160300 | 8/2020 | | |
| WO | WO-2020160300 A2 * | 8/2020 | .......... | C12Q 1/6869 |
| WO | WO-2020160300 A9 | 10/2020 | | |
| WO | WO 2020/257654 | 12/2020 | | |
| WO | WO-2020243207 A1 | 12/2020 | | |
| WO | WO 2021/163275 | 8/2021 | | |
| WO | WO 2021/173681 | 9/2021 | | |
| WO | WO 2021/222791 | 11/2021 | | |

OTHER PUBLICATIONS

Shang L., et al., "Electrical Characterization of Nanowire Bridges Incorporating Biomolecular Recognition Elements", Nanotechnology, vol. 16, 2005, pp. 2846-2851.
Zhang B., et al., "Engineering an Enzyme for Direct Electrical Monitoring of Activity", ACS Nano, vol. 14, No. 2, Oct. 2019, 1360-1368, 14 Pages, XP055736319, US ISSN: 1936-0851, DOI: 10.1021/acsnano.9b06875.
Ackerman et al., Massively multiplexed nucleic acid detection with Cas13. Nature. Jun. 2020;582(7811):277-282.
Adhikari et al., Conductivity of individual Geobacter pili. RSC Advances, 2016. 6: p. 8354-8357.
Alloway et al., Interface Dipoles Arising from Self-Assembled Monolayers on Gold: UV-Photoemission Studies of Alkanethiols and Partially Fluorinated Alkanethiols. J. Phys. Chem. B 2003, 107:11690-11699.
Altschul et al., Basic local alignment search tool. J Mol Biol. Oct. 5, 1990;215(3):403-10.
Altschul et al., Gapped BLAST and PSI-BLAST: a new generation of protein database search programs. Nucleic Acids Res. Sep. 1, 1997;25(17):3389-402.
Amdursky et al., Electronic transport via proteins. Adv Mater. Nov. 12, 2014;26(42):7142-61.
Amdursky et al., Solid-state electron transport via cytochrome c depends on electronic coupling to electrodes and across the protein. PNAS, Apr. 15, 2014, vol. 111, No. 15, pp. 5556-5561.
Artes et al., Transistor-like Behavior of Single Metalloprotein Junctions. Nano Lett.,2012, 12(6), pp. 2679-2684 (publication date (Web): Oct. 5, 2011).
Aubert et al., Intraprotein radical transfer during photoactivation of DNA photolyase. Nature. Jun. 1, 2000;405(6786):586-90.
Ausubel et al. Current Protocols in Molecular Biology, John Wiley & Sons, New York, 1998.
Bostick et al., Protein bioelectronics: a review of what we do and do not know. Rep Prog Phys. Feb. 2018;81(2):026601. 58 pages.

Chang et al., Chemical recognition and binding kinetics in a functionalized tunnel junction. Nanotechnology. Jun. 15, 2012;23(23):235101. 28 pages.
Chen, Y.-S., et al., "DNA sequencing using electrical conductance measurements of a DNA polymerase," Nature Nanotechnology, May 5, 2013, pp. 1-7; https://doi.org/10.1038/nnano.2013.71.
Chichil et al., Linkers in the structural biology of protein-protein interactions. Protein Sci. Feb. 2013;22(2):153-67.
Chin et al., Addition of p-Azido-I-phenylalanine to the Genetic Code of Escherichia coli. J. Am. Chem. Soc. 2002. 124,31, 9026-9027.
Choi et al. "Site-specific inhibition of integrin alpha v beta 3-vitronectin association by a serasp-val sequence through an Arg-Gly-Asp-binding site of the integrin." Proteomics, vol. 10, Issue 1, No. Jan. 1, 2010, pp. 72-80 (First published Oct. 30, 2009).
Choi et al., "Single-Molecule Lysozyme Dynamics Monitored by an Electronic Circuit," Science (2012) 335:319-324; DOI: 10.1126/science.1214824.
Cui et al., Reproducible measurement of single-molecule conductivity. Science. Oct. 19, 2001;294(5542):571-4.
Dellafiore et al., Modified Nucleoside Triphosphates for In-vitro Selection Techniques. Front Chem. May 4, 2016;4:18.
Duffy et al., Modified nucleic acids: replication, evolution, and next-generation therapeutics. BMC Biology, Sep. 2, 2020. 18:112. 14 pages.
Extended European Search Report for PCT/US2019031394. Mailed Jan. 5, 2022. 7 pages.
Fairhead et al., Plug-and-play pairing via defined divalent streptavidins. J Mol Biol. Jan. 9, 2014;426(1):199-214.
Fujino et al, Chimeric RNA Oligonucleotides Incorporating Triazole-Linked Trinucleotides: Synthesis and Function as mRNA in Cell-Free Translation Reactions. J Org Chem. Oct. 7, 2016;81(19):8967-8976.
Fulton et al., Purification of monoclonal antibody against Ebola GP1 protein expressed in Nicotiana benthamiana. J Chromatogr A. Apr. 10, 2015;1389:128-32.
Garg et al., Interface Electrostatics Dictates the Electron Transport via Bioelectronic Junctions. ACS Appl Mater Interfaces. Dec. 5, 2018;10(48):41599-41607.
Giese et al., Direct observation of hole transfer through DNA by hopping between adenine bases and by tunnelling. Nature. Jul. 19, 2001;412(6844):318-20.
Giese et al., Long distance charge transport through DNA: quantification and extension of the hopping model. Chemphyschem. Dec. 15, 2000;1(4):195-8.
Gonnet et al., Exhaustive matching of the entire protein sequence database. Science. Jun. 5, 1992;256(5062):1443-5.
Guo et al., Tuning electronic transport via hepta-alanine peptides junction by tryptophan doping. Proc Natl Acad Sci U S A. Sep. 27, 2016;113(39):10785-90.
Hajian et al., Detection of unamplified target genes via CRISPR-Cas9 immobilized on a graphene field-effect transistor. Nat Biomed Eng. Jun. 2019;3(6):427-437.
Harriman. Further comments on the redox potentials of tryptophan and tyrosine. Journal of Physical Chemistry 1987. 91:6102-6104.
Hohl et al. Engineering a Polyspecific Pyrrolysyl-tRNA Synthetase by a High Throughput FACS Screen. Sci Rep. Aug. 19, 2019;9(1):11971.
International Search Report and Written Opinion for PCT/US19/31394. Mailed Sep. 10, 2019. 11 pages.
International Search Report and Written Opinion for PCT/US20/15931. Mailed Jul. 27, 2020. 17 pages.
International Search Report and Written Opinion for PCT/US20/38740. Mailed Oct. 2, 2020. 14 pages.
International Search Report and Written Opinion for PCT/US21/17583. Mailed May 3, 2021. 9 pages.
International Search Report and Written Opinion for PCT/US21/19428. Mailed May 6, 2021. 25 pages.
International Search Report and Written Opinion for PCT/US21/27650. Mailed Aug. 25, 2021. 9 pages.
International Search Report and Written Opinion for PCT/US21/30239. Mailed Sep. 27, 2021. 10 pages.
International Search Report and Written Opinion for PCT/US21/34698. Mailed Sep. 30, 2021. 10 pages.

(56)        References Cited

OTHER PUBLICATIONS

International Search Report and Written Opinion for PCT/US21/63851. Mailed Feb. 17, 2022. 9 pages.
International Search Report and Written Opinion for PCT/US21/64905. Mailed Mar. 17, 2022. 9 pages.
Jeffrey, An Introduction to Hydrogen Bonding. Oxford University Press New York. 1997. TOC only. 6 pages.
Kluenker et al., Monitoring Thiol-Ligand exchange on Au nanoparticle surfaces. Langmuir. Jan. 30, 2018;34(4):1700-1710.
Kotlowski Fine discrimination of volatile compounds by graphene-immobilized odorant-binding proteins, Sensors and Actuatores B: Chemical 2018 (256): 564-72.
Kyte et al., A simple method for displaying the hydropathic character of a protein. J Mol Biol. May 5, 1982;157(1):105-32.
Lagunas et al., Long distance electron transfer through the aqueous solution between redox partner proteins. Nat Commun. Dec. 4, 2018;9(1):5157.
Lai et al., Monoclonal antibody produced in plants efficiently treats West Nile virus infection in mice. Proc Natl Acad Sci U S A. Feb. 9, 2010;107(6):2419-24.
Lai et al., Robust production of virus-like particles and monoclonal antibodies with geminiviral replicon vectors in lettuce. Plant Biotechnol J. Jan. 2012;10(1):95-104.
Leary et al., Unambiguous one-molecule conductance measurements under ambient conditions. Nano Lett. Jun. 8, 2011;11(6):2236-41.
Li et al., CRISPR-SE: a brute force search engine for CRISPR design. NAR Genom Bioinform. Feb. 23, 2021;3(1):lqab013.
Li et al., Synthesis and Photovoltaic effect on electron-withdrawing units for low band gap conjugated polymers bearing bi(thienylenevinylene) side chains. Polymers. 2019, vol. 11 iss 9 pp. 1-13.
Lindsay. Ubiquitous Electron Transport in Non-Electron Transfer Proteins. Life (Basel). May 20, 2020;10(5):72. 13 pages.
Liu et al., Vertical T cellimmunodomincance and epitope entropy determine HIV-1 escape. J Clin Invest. Jan. 2013;123(1):380-93.
Main et al., Design of stable alpha-helical arrays from an idealized TPR motif. Structure. May 2003;11(5):497-508.
Malvankar et al., Tunable metallic-like conductivity in microbial nanowire networks. Nat Nanotechnol. Aug. 7, 2011;6(9):573-9.
Marakova et al., An updated evolutionary classification of CRISPR-Cas systems. Nat Rev Microbiol. Nov. 2015;13(11):722-36.
Mckenzie et al., Recent progress in non-native nucleic acid modifications. Chem Soc Rev. Apr. 26, 2021;50(8):5126-5164.
Mejias et al., Controlled nanometric fibers of self-assembled designed protein scaffolds. Nanoscale. Oct. 7, 2014;6(19):10982-8.
Metsky et al., Diagnostic design with machine learning model-based optimization. bioRxiv 2020.11.28.401877: 95 pages.
Mullegama et al., Nucleic Acid Extraction from Human Biological Samples. Methods Mol Biol 2019;1897:359-383.
Nitzan. Chemical dynamics in condensed phases. Oxford University Press., Oxford. 2006. TOC only. 13 pages.
Odella et al., Controlling Proton-Coupled Electron Transfer in Bioinspired Artificial Photosynthetic Relays. J Am Chem Soc. Nov. 14, 2018;140(45):15450-15460.
Olsen et al., "Electronic Measurements of Single-Molecule Processing by DNA Polymerase I (Klenow Fragment)," Journal of the American Chemical Society (Apr. 30, 2013); pp. 1-12; DOI: 10.1021/ja311603r.
Pang et al. "Fixed-Gap Tunnel Junction for Reading DNA Nucleotides" ACS Nano, 2014, 8(12), pp. 11994-12003 (Publication Date (Web): Nov. 7, 2014).
Pearson. Using the FASTA program to search protein and DNA sequence databases. Methods Mol Biol. 1994;24:307-31.
Quast et al., Cotranslational incorporation of non-standard amino acids using cell-free protein synthesis. FEBS Lett. Jul. 8, 2015;589(15):1703-12.
Ruiz et al., Bioengineering a Single-Protein Junction. J Am Chem Soc. Nov. 1, 2017;139(43):15337-15346.

Sambrook et al., Molecular Cloning: A Laboratory Manual, 3d ed., Cold Spring Harbor Press, 2001. TOC only. 23 pages.
Sano et al., Cooperative biotin binding by streptavidin. Electrophoretic behavior and subunit association of streptavidin in the presence of 6 M urea. J Biol Chem. Feb. 25, 1990;265(6):3369-73.
Seifert, Characterization of Streptavidin Binding to Biotinylated, Binary Self-Assembled Thio Monolayers-Influence of Component Ratio and Solvent, Langmuir, 2010, 26(9): 6386-93.
Sek et al., Conductance of alpha-helical peptides trapped within molecular junctions. J Phys Chem B. Oct. 5, 2006;110(39):19671-7.
Sequences of amino acids as found on the world wide web at bmrb.wisc.edu/referenc/choufas. 4 pages.
Smith. The hydrophilic nature of a clean gold surface. J. Colloid Interface Science 1980. 75:51-55.
Staals et al., RNA targeting by the type III-A CRISPR-Cas Csm complex of Thermus thermophilus. Mol Cell. Nov. 20, 2014;56(4):518-30.
Tripkovic et al., Standard hydrogen electrode and potential of zero charge in density functional calculations. Phys. Rev. B 2011. 84:115452.
Tuchband et al., Insulated gold scanning tunneling microscopy probes for recognition tunneling in an aqueous environment. Rev Sci Instrum. Jan. 2012;83(1):015102.
Vaish et al., A novel, modification-dependent ATP-binding aptamer selected from an RNA library incorporating a cationic functionality. Biochemistry. Jul. 29, 2003;42(29):8842-51.
Vattay et al., Quantum Criticality at the Origin of Life. Journal of Physics: Conference Series 2015. 626: p. 012023. 11 pages.
Willner et al., Mediated electron transfer in glutathione reductase organized in self-assembled monolayers on Au electrodes. J. Am. Chem. Soc., 1992. 114: p. 10965-10966.
Xiao et al., Conductance titration of single-peptide molecules. J Am Chem Soc. May 5, 2004;126(17):5370-1.
Yang et al., Plant-produced Zika virus envelope protein elicits neutralizing immune responses that correlate with protective immunity against Zika virus in mice. Plant Biotechnol J. Feb. 2018;16(2):572-580.
Zhang et al., Engineering an Enzyme for Direct Electrical Monitoring of Activity. ACS Nano. Feb. 25, 2020;14(2):1360-1368.
Zhang et al., Electronic Conductance Resonance in Non-Redox-Active Proteins. J Am Chem Soc. Apr. 1, 2020;142(13):6432-6438.
Zhang et al., Electronic Decay Length in a Protein Molecule. Nano Lett. Jun. 12, 2019;19(6):4017-4022.
Zhang et al., Observation of Giant Conductance Fluctuations in a Protein. Nano Futures. 2017;1(3):035002. 25 pages.
Zhang et al., Role of contacts in long-range protein conductance. Proc Natl Acad Sci U S A. Mar. 26, 2019;116(13):5886-5891.
Zwolak et al. "Electronic Signature of DNA Nucleotides via Transverse Transport" NanoLett., 2005, 5(3), pp. 421-424 (Publication Date (Web): Feb. 12, 2005).
Anzai J-I., et al., Avidin-biotin Complexation for Enzyme Sensor Applications, Trends in Analytical Chemistry, 1994, vol. 13, No. 5, pp. 205-210.
Arielly R., et al., Real-Time Detection of Redox Events in Molecular Junctions, Journal of the American Chemical Society, Jan. 27, 2014, vol. 136, No. 6, pp. 2674-2680.
Artes J.M., et al., Conductance Switching in Single Wired Redox Proteins, Small, Jul. 9, 2014, vol. 10, No. 13, pp. 2537-2541, Published Online: Mar. 13, 2014.
Barhoumi H., et al., Urease Immobilization on Biotinylated Polypyrrole Coated ChemFEC Devices for Urea Biosensor Development, IRBM, Apr. 1, 2008, vol. 29, No. 2-3, pp. 192-201 (10 Pages).
Bayer E.A., et al., 3-(N-Maleimido-Propionyl) Biocytin: A Versatile Thiol-Specific Biotinylating Reagent, Analytical Biochemistry, Academic Press, Amsterdam, NL, Sep. 1, 1985, vol. 149, No. 2, pp. 529-536, DOI: 10.1016/0003-2697(85)90609-8, ISSN: 0003-2697, XP024823414, [Retrieved on Sep. 1, 1985].
Beratan D.N., et al., Charge Transfer in Dynamical Biosytems, or The Treachery of (Static) Images, Accounts of Chemical Research, Feb. 17, 2015, vol. 48, No. 2, pp. 474-481, (Published on: Oct. 13, 2014).

(56)         References Cited

OTHER PUBLICATIONS

Bertazzon A., et al., Scanning Tunneling Microscopy Imaging of Torpedo Acetylcholine Receptor, Proceedings of the National Academy of Sciences, USA, Oct. 15, 1992, vol. 89, No. 20, pp. 9632-9636.

Bogomolny E., et al., Structure of Wave Functions of Pseudointegrable Billiards, Physical Review Letters, Jun. 18, 2004, vol. 92, No. 24, pp. 244102-1-1244102-4, (Published on: Jun. 16, 2004).

Bogomolny E.B., et al., Models of Intermediate Spectral Statistics, Physical Review E, Feb. 1, 1999, vol. 59, No. 2, pp. R1315-R1318.

Carter N.A., et al., Functional Protein Materials: Beyond Elastomeric and Structural Proteins, Polymer Chemistry, May 6, 2019, vol. 10, pp. 2952-2959.

Castellarnau M., et al., Integrated Microanalytical System Based on Electrochemical Detection and Cell Positioning, Materials Science and Engineering, Mar. 2006, vol. 26, No. 2-3, pp. 405-410.

Chang S., et al., Gap Distance and Interactions in a Molecular Tunnel Junction, Journal of American Chemical Society, 2011, vol. 133, No. 36, pp. 14267-14269, (Published on Aug. 12, 2011).

Chang S., et al., Palladium Electrodes for Molecular Tunnel Junctions, Nanotechnology, Oct. 4, 2012, vol. 23, No. 42(425202), pp. 1-5, 6 Pages.

Chen X., Palladium as electrode in DNA sequencing, Applied Physics Letters, Aug. 9, 2013, vol. 103, No. 063306, pp. 1-4 (5 Pages).

Chen Y-S., et al., A Protein Transistor Made of an Antibody Molecule and Two Gold Nanoparticles, Nature Nanotechnology, Mar. 2012, vol. 7, pp. 197-203 (25 Pages), (Published Online on: Feb. 26, 2012).

Co-Pending U.S. Appl. No. 62/184,776, filed Jun. 25, 2015, 24 Pages.

Cui X., et al., Layer-by-layer 1 Assembly of Multilayer Filme Composed of Avidin and Biotin-labeled Antibody for Immunosensing, Biosensors And Bioelectronics, Jan. 1, 2003, vol. 18, No. 1, pp. 59-67.

Dong X., et al., (Alphav)(Beta3) Integrin Crystal Structures and Their Functional Implications, Biochemistry, Oct. 29, 2012, vol. 51, No. 44, pp. 8814-8828.

Engel G.S., et al., Evidence for Wavelike Energy Transfer Through Quantum Coherence in Photosynthetic Systems, Nature, Apr. 12, 2007, vol. 446, No. 7137, pp. 782-786.

Fan F-R.F., et al., Electrochemical Detection of Single Molecules, Science, Feb. 10, 1995, vol. 267, No. 5199, pp. 871-874 (5 Pages).

Gerrits M., et al., Cell-Free Synthesis of Defined Protein Conjugates by Site directed Cotranslational Labeling, NCBI Bookshelf, Madame Curie Bioscience Database [Internet]. Austin (TX) Landes Bioscience; 2000-2013, Jan. 1, 2013, 12 Pages, Retrieved from URL:https://ww.ncbi.nlm.nih.gov/books/NBK 6497.

Grden M., et al., Electrochemical Behaviour of Palladium Electrode: Oxidation, Electrodissolution and Ionic Adsorption, Electrochimica Acta, Nov. 1, 2008, vol. 53, No. 26, pp. 7583-7806, 16 Pages.

Haiss W., et al., Thermal Gating of the Single Molecule Conductance of Alkanedithiols, Faraday Discussions, 2006, vol. 131, pp. 253-264, (Published on Oct. 4, 2005).

Hays H.C.W., et al., Development of Capacitance Based Immunosensors on Mixed Self-assembled Monolayers, Sensors and Actuators B: Chemical, Apr. 26, 2006, vol. 114, No. 2, pp. 1064-1070.

Hoffman R., et al., An Extended Huckel Theory I. Hydrocarbons, The Journal of Chemical Physics, Sep. 15, 1963, vol. 39, No. 6, pp. 1397-1412 (17 Pages).

Holzel R., et al., Trapping Single Molecules by Dielectrophoresis, Physical Review Letters, Sep. 16, 2005, vol. 95, pp. 128012-1-128012-4 (4 Pages), (Published on Sep. 13, 2005).

Ihalainen P., et al., Application of Paper-supported Printed Gold Eletrodes for Impedimetric Immunosensor Development, Biosensors, 2013, vol. 3, pp. 1-17.

Im J.O., et al., Electronic Single-molecule Identification of Carbohydrate Isomers by Recognition Tunnelling, Nature Communications, Dec. 21, 2016, vol. 7, Article 13868, pp. 1-7.

Karachaliou C-E., et al., IgY Technology: Methods for Developing and Evaluating Avian Immunoglobulins for the in Vitro Detection of Biomolecules, World Journal of Methodology, Sep. 20, 2021, vol. 11, No. 5, pp. 243-262 (24 Pages).

Krishnan S., et al., Long-Range Conductivity in Proteins Mediated by Aromatic Residues, ACS Physical Chemistry Au, Jun. 2, 2023, vol. 3, pp. 444-455.

Kumar K.S., et al., Long-range Tunneling Processes Across Ferritin-based Junctions, Advanced Materials, Mar. 2, 2016, vol. 28, No. 9, pp. 1824-1830, (Dec. 28, 2015).

Leatherbarrow R.J., et al., Structure of Immunoglobulin G by Scanning Tunnelling Microscopy, Journal of Molecular Biology, Sep. 20, 1991, vol. 221, No. 2, pp. 361-365.

Lindsay S., et al., Recognition Tunneling, Nanotechnology, Jun. 4, 2010, vol. 21, No. 26, (262001), pp. 1-12 (13 Pages).

Lloyd S., Quantum Coherence in Biological Systems, Journal of Physics: Conference Series, 2011, vol. 302, No. 012037, pp. 1-5 (6 Pages).

Lucie S., et al., Clustering and Internalization of Integrin (Alphav)(Beta3) With a Tetrameric RGD-synthetic Peptide, Molecular Therapy, May 2009, vol. 17, No. 5, pp. 837-843, (Published Online on Mar. 3, 2009).

Luo B-H., et al., Structural Basis of Integrin Regulation and Signaling, Annual Review of Immunology, 2007, vol. 25, pp. 619-647 (32 Pages), (Jan. 2, 2007).

Maalouf R., et al., Label-Free Detection of Bacteria by Electrochemical Impedance Spectroscopy: Comparison to Surface Plasmon Resonance, Analytical Chemistry, May 25, 2007, vol. 79, No. 13, pp. 4879-4886.

Miodek A., et al., Streptavidin-Polypyrrole Film as Platform for Biotinylated Redox Probe Immobilization for Electrochemical Immunosensor Application, Electroanalysis, 2016, vol. 28, No. 8, pp. 1824-1832, (Published Online on May 27, 2016).

Nature: Protein Structure Nature Education at the Scitable by Nature Education, 2014, 4 Pages, [Retrieved on Oct. 15, 2024] Retrieved from URL: https://www.nature.com/scitable/topicpage/protein-structure-14122136/.

Non-Final Office Action for U.S. Appl. No. 15/375,901, mailed Dec. 10, 2018, 30 Pages.

Notice of Allowance for U.S. Appl. No. 15/375,901, mailed Mar. 29, 2019, 11 Pages.

O'Boyle N.M., et al., Open Babel: An Open Chemical Toolbox, Journal of Cheminformatics, Oct. 7, 2011, vol. 3, No. 33, pp. 1-14.

Onuchic J.N., et al., Pathway Analysis of Protein Electron-Transfer Reactions, Annual Review of Biophysics and Biomolecular Structure, 1992, vol. 21, pp. 349-377 (31 Pages).

Ouerghi O., et al., Impedimetric Immunosensor Using Avidin-biotin for Antibody Immobilization, Bioelectrochemistry, May 15, 2002, vol. 56, No. 1-2, pp. 131-133.

Palecek E., et al., Electrochemistry of Nonconjugated Proteins and Glycoproteins. Toward Sensors for Biomedicine and Glycomics, Chemical Reviews, 2015, vol. 115, No. 5, pp. 2045-2108, (Published on Feb. 9, 2015).

Pang P., et al., Fixed-gap Tunnel Junction for Reading DNA Nucleotides, ACS Nano, Nov. 7, 2014, vol. 8, No. 12, pp. 11994-12003 (20 Pages), (Including Supporting Material).

Polizzi N.F., et al., Physical Constraints on Charge Transport Through Bacterial Nanowires, Faraday Discussions, 2012, vol. 155, pp. 43-62, (Published on Oct. 17, 2011).

Prodromidis M.I., Impedimetric Immunosensors—A Review, Electrochimica Acta, May 30, 2010, vol. 55, No. 14, pp. 4227-4233.

Roxin A., et al., Flexible or Fixed: A Comparative Review of Linear and Cyclic Cancer-Targeting Peptides, Future Medicinal Chemistry, Aug. 2012, vol. 4, No. 12, pp. 1601-1618.

Sadar J., Top-Down and Bottom-Up Strategies to Prepare Nanogap Sensors for Controlling and Characterizing Single Biomolecules, Arizona State University, Aug. 2019, 160 Pages, Approved Jul. 2019.

Sela-Culang I., et al., The Structural Basis of Antibody-Antigen Recognition, Frontiers in Immunology, Oct. 8, 2013, vol. 4, Article No. 302, 13 Pages, DOI: 10.3389/fimmu.2013.00302, PMID: 24115948, PMCID: PMC3792396.

(56)           References Cited

OTHER PUBLICATIONS

Shimura K., et al., Heterogeneous Photocatalytic Hydrogen Production From Water and Biomass Derivatives, Energy Environmental Science, 2011, vol. 4, pp. 2467-2481.

Simmons J.G., Generalized Formula for the Electric Tunnel Effect Between Similar Electrodes Separated by a Thin Insulating Film, Journal of Applied Physics, Jun. 1963, vol. 34, No. 6, pp. 1793-1803 (12 Pages).

Stuchebrukhov A.A., Toward AB Initio Theory of Long-Distance Electron Tunneling in Proteins: Tunneling Currents Approach, Advances in Chemical Physics, Jan. 1, 2001, vol. 118, pp. 1-44.

Thomson N.H., et al., Molecular Images of Cereal Proteins by STM, Ultramicroscopy, Jul. 1992, vol. 42-44, (Part B), pp. 1204-1213.

Uygun Z.O., et al., CRISPR-dCAS9 Powered Impedimetric Bioscensor for Label-free Detection of Circulating Tumor DNAs, Analytica Chimica Acta, 2020, vol. 1121, pp. 35-41.

Varga J.M., et al., Binding of a Mouse Monoclonal IgE (anti-DNP) Antibody to Radio-derivatized Polystyrene-DNP Complexes, The FASEB Journal, Federation of American Societies for Experimental Biology, Jun. 1, 1990, vol. 4, No. 9, pp. 2678-2683.

Xiong J-P., et al., Crystal Structure of the Extracellular Segment of Integrin (Alpha)v(Beta)3 in Complex With an Arg-gly-asp Ligand, Science, Apr. 5, 2002, vol. 296, No. 5565, pp. 151-155 (6 Pages), (Published Online on Mar. 7, 2002).

Yoon B-J., Hidden Markov Models and their Applications in Biological Sequence Analysis, Current Genomics, 2009, vol. 10, No. 6, pp. 402-415.

Zhang B., et al., Electronic Transport in Molecular Wires of Precisely Controlled Length Built from Modular Proteins, ACS Nano Journal, Jan. 14, 2022, vol. 16, No. 1, pp. 1671-1680 (10 Pages).

Zhang B., et al., Observation of Giant Conductance Fluctuations in a Protein, Nano Futures, 2017, vol. 1, pp. 1-15.

Zhang Y., et al., Biological Charge Transfer via Flickering Resonance, Proceedings of the National Academy of Sciences, USA, Jul. 15, 2014, vol. 111, No. 28, pp. 10049-10054, (Published Online: Jun. 25, 2014).

Cecchetelli A., "Methods for Biotinylating Your Macromolecule of Interest", Plasmids101: Biotinylation, Nov. 15, 2018, pp. 1-12.

* cited by examiner

Peak1 = 0.39 nS
Peak2 = 3.64 nS
Peak3 = 15.14 nS

Peak1 = 0.30 nS
Peak2 = 2.62 nS
Peak3 = 11.22 nS

METHODS FOR SEQUENCING BIOPOLYMERS

RELATED APPLICATIONS

This application claims priority to and the benefit of U.S. Provisional Patent Application No. 63/197,901 filed Jun. 7, 2021, which is incorporated herein by reference in its entirety for all purposes.

GOVERNMENT SUPPORT

This invention was made with government support under R01 HG011079 awarded by the National Institutes of Health. The government has certain rights in the invention.

FIELD

The present disclosure provides devices, systems, and methods related to sequencing a biopolymer. In particular, the present disclosure relates to methods for sequencing a polynucleotide using a bioelectronic device that includes protein assemblies used as coupling molecules in bioelectronic circuits. The present disclosure also provides multimeric protein assemblies with various combinations of live and dead subunits arranged to maximize conduction.

BACKGROUND

Proteins connected to electrodes via well-defined chemical contacts are remarkably good electrical conductors. Their contact resistance is high, probably owing to the tunnel barrier presented by an outer shell of hydrated residues, but once carriers are injected, the long decay length (on the order of 10 nm) gives rise to improved conductance relative to conventional molecular wires, for lengths in excess of 5 nm. The specific self-assembly of proteins allows quite complex circuits to be built. For example, because polymerase Φ29 interacts with metals unpredictably owing to seven surface cysteines, streptavidin bridges were used to connect doubly-biotinylated Φ29 to biotinylated electrodes, allowing enzyme fluctuations to be recorded electrically. Streptavidin is a tetrameric protein with an extremely high affinity for biotin, and it is an important component of nano-scale protein assemblies. The chemical nature of the electrical contact has a strong effect on the conductance of streptavidin. Streptavidin molecules connected to electrodes via surface thiols (by means of lysine modification) have a significantly lower conductance than molecules attached to electrodes by means of the non-covalent biotin-streptavidin interaction, despite an eight-atom saturated chain linker between the biotin and the electrode. However, the distribution of measured conductances for streptavidin molecules (and complexes connected via streptavidin) has multiple peaks, indicative of multiple modes of connection, made possible by the tetravalent nature of streptavidin. This ambiguity in connection geometries is not easily resolved.

SUMMARY

Embodiments of the present disclosure include a bioelectronic device comprising a first electrode and a second electrode separated by a gap. In accordance with these embodiments, the bioelectronic device further comprises a protein attached to the first and second electrodes via a linker, and the linker includes an assembly of monomers comprising at least one ligand-binding monomer and at least one non-ligand-binding monomer. In some embodiments, the assembly of monomers are configured to maximize electronic conductance.

In some embodiments, the at least one ligand-binding monomer comprises two ligand-binding monomers. In some embodiments, the at least one ligand-binding monomer comprises three ligand-binding monomers. In some embodiments, the at least one non-ligand-binding monomer comprises two non-ligand-binding monomers.

In some embodiments, the assembly of monomers comprises two ligand-binding monomers arranged in trans. In some embodiments, the assembly of monomers comprises two ligand-binding monomers arranged in cis.

In some embodiments, the assembly of monomers comprises three ligand-binding monomers and exhibits a higher conductance compared to an assembly of monomers comprising two ligand-binding monomers.

In some embodiments, the linker comprises a peptide or polypeptide. In some embodiments, the linker comprises streptavidin.

In some embodiments, the linker further comprises a tag. In some embodiments, the tag comprises a negative charge. In some embodiments, the tag comprises at least one of a glutamate moiety and/or an aspartate moiety. In some embodiments, the tag comprises at least two glutamate moieties. In some embodiments, the tag comprises a hexaglutamate moiety. In some embodiments, the tag is coupled to the C-terminal end of each of the at least one ligand-binding monomers in the assembly.

In some embodiments, the ligand is biotin.

In some embodiments, the protein is biotinylated.

In some embodiments, the first and/or the second electrode comprises gold, palladium, platinum, silver, copper, or any alloys thereof.

In some embodiments, the protein is selected from the group consisting of a polymerase, a nuclease, a proteasome, a glycopeptidase, a glycosidase, a kinase and an endonuclease.

In some embodiments, the linker is attached to an inactive region of the protein.

Embodiments of the present disclosure also include a method of modulating electronic conductance through a protein using any of the devices described herein.

In some embodiments, modulating electronic conductance comprises increasing conductance using the assembly of monomers comprising at least one ligand-binding monomer and at least one non-ligand-binding monomer as compared to using an assembly of monomers that does not comprise at least one ligand-binding monomer and at least one non-ligand-binding monomer.

Embodiments of the present disclosure also include a method for sequencing a polynucleotide using a bioelectronic device. In accordance with these embodiments, the method includes (a) introducing a template polynucleotide to a bioelectronic device, wherein the bioelectronic device comprises a polymerase functionally coupled to at least one of a first electrode and a second electrode via a linker, wherein the linker comprises an assembly of monomers comprising at least one ligand-binding monomer and at least one non-ligand-binding monomer; (b) introducing a solution comprising four nucleotidepolyphosphate monomers to the device comprising the template polynucleotide; and (c) obtaining a bioelectronic signature of polymerase activity based on current fluctuations as each complementary nucleotidepolyphosphate monomer is incorporated into the template polynucleotide. In some embodiments, at least one characteristic of the bioelectronic signature identifies each of the complementary nucleotidepolyphosphate monomers incorporated into the template polynucleotide.

In some embodiments of the method, the at least one ligand-binding monomer comprises two ligand-binding monomers. In some embodiments of the method, the at least one ligand-binding monomer comprises three ligand-binding monomers. In some embodiments of the method, the at least one non-ligand-binding monomer comprises two non-ligand-binding monomers.

In some embodiments of the method, the assembly of monomers comprises two ligand-binding monomers arranged in trans. In some embodiments of the method, the assembly of monomers comprises two ligand-binding monomers arranged in cis.

In some embodiments of the method, the assembly of monomers comprises three ligand-binding monomers and exhibits a higher conductance compared to an assembly of monomers comprising two ligand-binding monomers.

In some embodiments of the method, the template polynucleotide is DNA.

In some embodiments of the method, the exonuclease activity of the polymerase is disabled.

In some embodiments of the method, the linker comprises a peptide or polypeptide. In some embodiments of the method, the linker comprises streptavidin.

In some embodiments of the method, the polymerase is biotinylated.

In some embodiments of the method, the linker is attached to a region of the polymerase that is inactive.

In some embodiments, the method comprises applying a voltage bias between the first and second electrodes that is 100 mV or less.

In some embodiments of the method, the linker further comprises a tag. In some embodiments of the method, the tag comprises a negative charge. In some embodiments of the method, the tag comprises at least one of a glutamate moiety and/or an aspartate moiety. In some embodiments of the method, the tag comprises at least two glutamate moieties. In some embodiments of the method, the tag comprises a hexaglutamate moiety. In some embodiments of the method, the tag is coupled to the C-terminal end of each of the at least one ligand-binding monomers in the assembly.

DETAILED DESCRIPTION

Figures 1A, 1B, 1C:
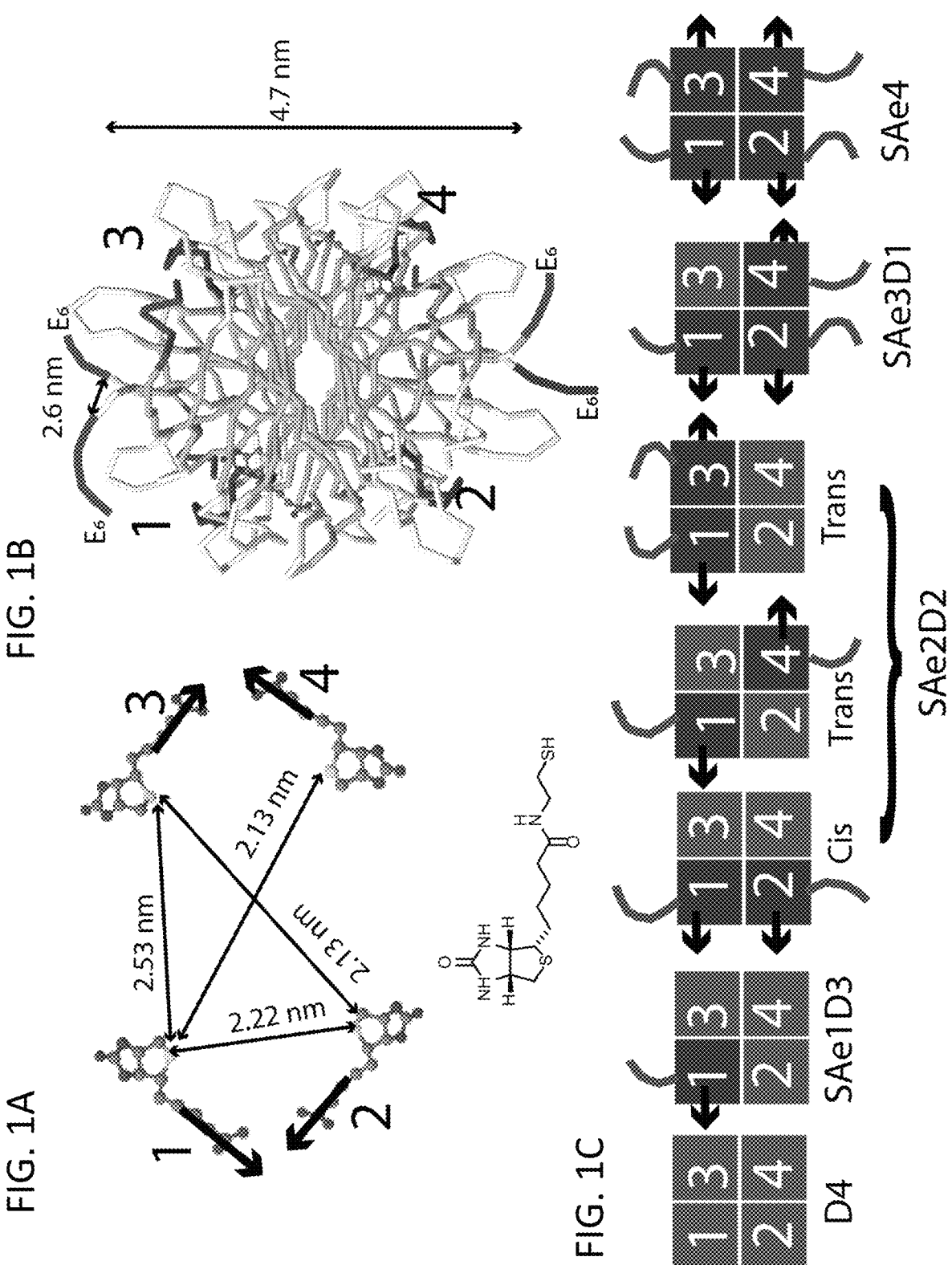
FIGS. 1A-1C: Streptavidin with a controlled ratio of live and dead units. Locations of the four biotins bound in the WT tetramer (note that in this 2D projection, the arrow lengths do not reflect true distances) (FIG. 1A). The thio-biotin used in the present disclosure is shown. Backbone structure of the tetramer in the same orientation; the approximate locations of the hexaglutamate tails in the SAe4 molecule is shown by the red lines labeled $E_6$ (FIG. 1B). Compositions of the reconstituted tetramers. Red=dead monomers, blue=live monomers, arrows=biotin tails, red lines=$E_6$ tails (FIG. 1C).

In the following detailed description, reference is made to the accompanying drawings that form a part hereof, and in which are shown by way of illustration embodiments that may be practiced. It is to be understood that other embodiments may be utilized and structural or logical changes may be made without departing from the scope. Therefore, the following detailed description is not to be taken in a limiting sense, and the scope of embodiments is defined by the appended claims and their equivalents.

Various operations may be described as multiple discrete operations in turn, in a manner that may be helpful in understanding embodiments; however, the order of description should not be construed to imply that these operations are order dependent.

Unless otherwise noted, technical terms are used according to conventional usage. Definitions of common terms in molecular biology can be found in Benjamin Lewin, Genes IX, published by Jones and Bartlet, 2008 (ISBN 0763752223); Kendrew et al. (eds.), The Encyclopedia of Molecular Biology, published by Blackwell Science Ltd., 1994 (ISBN 0632021829); and Robert A. Meyers (ed.), Molecular Biology and Biotechnology: a Comprehensive Desk Reference, published by VCH Publishers, Inc., 1995 (ISBN 9780471185710); and other similar references.

Suitable methods and materials for the practice or testing of this disclosure are described below. Such methods and materials are illustrative only and are not intended to be limiting. Other methods and materials similar or equivalent to those described herein can be used. For example, conventional methods well known in the art to which this disclosure pertains are described in various general and more specific references, including, for example, Sambrook et al., *Molecular Cloning: A Laboratory Manual,* 2d ed., Cold Spring Harbor Laboratory Press, 1989; Sambrook et al., *Molecular Cloning: A Laboratory Manual,* 3d ed., Cold Spring Harbor Press, 2001; Ausubel et al., *Current Protocols in Molecular Biology, Greene Publishing Associates,* 1992 (and Supplements to 2000); Ausubel et al., *Short Protocols in Molecular Biology: A Compendium of Methods from Current Protocols in Molecular Biology,* 4th ed., Wiley & Sons, 1999; Harlow and Lane, *Antibodies: A Laboratory Manual,* Cold Spring Harbor Laboratory Press, 1990; and Harlow and Lane, *Using Antibodies: A Laboratory Manual,* Cold Spring Harbor Laboratory Press, 1999. In addition, the materials, methods, and examples are illustrative only and not intended to be limiting.

Section headings as used in this section and the entire disclosure herein are merely for organizational purposes and are not intended to be limiting.

1. Definitions

To facilitate review of the various embodiments of the disclosure, the following explanations of specific terms are provided below. All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of" or, when used in the claims, "consisting of," will refer to the inclusion of exactly one element of a number or list of elements. In general, the term "or" as used herein shall only be interpreted as indicating exclusive alternatives (i.e., "one or the other but not both") when preceded by terms of exclusivity, such as "either," "one of" "only one of" or "exactly one of" "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

As used herein, "biological sample" generally refers to a biological specimen containing genomic DNA, RNA (such as mRNA), protein, or combinations thereof, obtained from a subject. Examples include, but are not limited to, saliva, peripheral blood, urine, tissue biopsy, surgical specimen, and autopsy material. In embodiments, the biological sample is a bodily fluid, such as blood, or a component thereof, such as plasma or serum.

As used herein, "biopolymer" generally refers to polymers (e.g., produced by living organisms or synthetically generated). Biopolymers contain monomeric units that are covalently bonded to form larger structures. There are three main classes of biopolymers, classified according to the monomeric units used and the structure of the biopolymer formed: polynucleotides (RNA and DNA), which are long polymers composed of 13 or more nucleotide monomers; polypeptides, which are short polymers of amino acids; and polysaccharides, which are often linear bonded polymeric carbohydrate structures. Other examples of biopolymers include rubber, suberin, melanin and lignin.

As used herein, an "isolated" biological component (e.g., such as a nucleic acid molecule, protein, or cell) has been substantially separated or purified away from other biological components in the cell of the organism, or the organism itself, in which the component naturally occurs, such as other chromosomal and extra-chromosomal DNA and RNA, proteins and cells. Nucleic acid molecules and proteins that have been "isolated" may be understood to have been purified by standard purification methods. The term also embraces nucleic acid molecules and proteins prepared by recombinant expression in a host cell as well as chemically synthesized nucleic acid molecules and proteins.

As used herein, "burst" generally refers to a section of a current stream in which the measured current changes between two levels more frequently relative to a pause, typically being in the high state for half the time of a pause. The measured current of the peaks in a burst is greater than about 20% of the baseline current passing through the molecule. Typically, a burst is observed when a nucleotide is being incorporated into a template sequence.

As used herein, "modification," "chemical modification," or "chemically modified" generally refers to any of a number of various processes involving the alteration of the chemical constituent or structure of molecules. For example, a polymerase can be chemically modified to form a chemical bond with a first electrode and a second electrode. In one example, a chemically-modified electrode is an electrode that has a surface chemically converted to change the electrode's properties, such as its physical, chemical, electrochemical, optical, electrical, and/or transport characteristics. As provided herein, the chemical modification can also involve chemically altering a polymerase so that it is compatible with a linker that binds to an electrode (e.g., biotin/streptavidin, HaloTag, and the like). In other embodiments, a modification can be generated via protein synthesis. For example, a polymerase can be designed to comprise one or more modifications (e.g., a linker) when synthesized from a polynucleotide that encodes the protein and the modification.

As used herein, "contact" and "contacting" can include placement in direct physical association, including both a solid and liquid form. "Contacting" can include a specific chemical contact between two different substances (e.g., covalent bond, or non-covalent bond having specific ligand interaction with specific amino acid residues).

As used herein, "complementarity" or "complementary" generally refers to the ability of a nucleic acid to form hydrogen bond(s) with another nucleic acid sequence by either traditional Watson-Crick base pairing or other non-traditional types. A percent complementarity indicates the percentage of residues in a nucleic acid molecule which can form hydrogen bonds (e.g., Watson-Crick base pairing) with a second nucleic acid sequence (e.g., 5, 6, 7, 8, 9, 10 out of 10 being 50%, 60%, 70%, 80%, 90%, and 100% complementary). "Perfectly complementary" generally indicates that all the contiguous residues of a nucleic acid sequence will hydrogen bond with the same number of contiguous residues in a second nucleic acid sequence. "Substantially complementary" as used herein refers to a degree of complementarity that is at least 60%, 65%, 70%, 75%, 80%, 85%, 90%, 95%, 97%, 98%, 99%, or 100% over a region of 8, 9, 10, 11, 12, 13, 14, 15, 16, 17, 18, 19, 20, 21, 22, 23, 24, 25, 30, 35, 40, 45, 50, or more nucleotides, or refers to two nucleic acids that hybridize under stringent conditions.

As used herein, "current stream" generally refers to a current signal generated over time, such as from the bioelectronic devices of the present disclosure.

As used herein, a "label" generally refers to an agent capable of detection, for example by ELISA, spectrophotometry, flow cytometry, or microscopy. For example, a label can be attached to a nucleic acid molecule or protein (indirectly or directly), thereby permitting detection of the nucleic acid molecule or protein. Examples of labels include, but are not limited to, radioactive isotopes, enzyme substrates, co-factors, ligands, chemiluminescent agents, fluorophores, haptens, enzymes, and combinations thereof. Methods for labeling and guidance in the choice of labels appropriate for various purposes are discussed for example in Sambrook et al. (Molecular Cloning: A Laboratory Manual, Cold Spring Harbor, New York, 1989) and Ausubel et al. (In Current Protocols in Molecular Biology, John Wiley & Sons, New York, 1998).

As used herein, the term "linker" or "linked" means joined together, either directly or indirectly. For example, a first moiety may be covalently or noncovalently (e.g., electrostatically) linked to a second moiety. This includes, but is not limited to, covalently bonding one molecule to another molecule, noncovalently bonding one molecule to another (e.g., electrostatically bonding), non-covalently bonding one molecule to another molecule by hydrogen bonding, non-covalently bonding one molecule to another molecule by van der Waals forces, and any and all combinations of such couplings. Indirect attachment is possible, such as by using a "linker" (a molecule or group of atoms positioned between two moieties). In several embodiments, linked components are associated in a chemical or physical manner so that the components are not freely dispersible from one another. For example, two components may be covalently bound to one another so that the two components are incapable of separately dispersing or diffusing. In several embodiments, linked components are associated in a chemical or physical manner so that the components are not freely dispersible from one another. For example, two components may be covalently bound to one another so that the two components are incapable of separately dispersing or diffusing.

As used herein, the terms "non-naturally occurring" and "engineered" interchangeably indicate the involvement of the hand of man. These terms, when referring to nucleic acid molecules or polypeptides, generally indicate that the nucleic acid molecule or the polypeptide is at least substantially free from at least one other component with which they are naturally associated in nature and as found in nature.

As used herein, "nucleic acid" generally refers to a deoxyribonucleotide or ribonucleotide polymer, which can include analogues of natural nucleotides that hybridize to nucleic acid molecules in a manner similar to naturally occurring nucleotides. In one example, a nucleic acid molecule is a single stranded (ss) DNA or RNA molecule, such as a probe or primer. In another example, a nucleic acid molecule is a double stranded (ds) nucleic acid. In another example, a nucleic acid is a modified DNA or RNA molecule, such as a xenonucleic acid (XNA). The term "nucleotide" generally refers to a base-sugar-phosphate combination and includes ribonucleoside triphosphates ATP, UTP, CTG, GTP and deoxyribonucleoside triphosphates such as dATP, dCTP, dITP, dUTP, dGTP, dTTP, or derivatives thereof. As described further herein, a nucleic acid can include deoxynucleotidepolyphosphate monomers (dNxPs), such as those having altered charges as compared to their corresponding standard deoxynucleotidetriphosphate monomers.

As used herein, "polypeptide," "peptide," and "protein" generally refer to a polymer in which the monomers are amino acid residues that are joined together through amide bonds. When the amino acids are alpha-amino acids, either the L-optical isomer or the D-optical isomer can be used, the L-isomers being preferred in nature. The term polypeptide is specifically intended to cover naturally occurring proteins, as well as those that are recombinantly or synthetically produced. A substantially purified polypeptide as used herein refers to a polypeptide that is substantially free of other proteins, lipids, carbohydrates or other materials with which it is naturally associated. In one embodiment, the polypeptide is at least 50%, for example at least 80% free of other proteins, lipids, carbohydrates or other materials with which it is naturally associated. In another embodiment, the polypeptide is at least 90% free of other proteins, lipids, carbohydrates or other materials with which it is naturally associated. In yet another embodiment, the polypeptide is at least 95% free of other proteins, lipids, carbohydrates or other materials with which it is naturally associated.

Conservative amino acid substitution tables providing functionally similar amino acids are well known to one of ordinary skill in the art. The following six groups are examples of amino acids that are considered to be conservative substitutions for one another: 1) Alanine (A), Serine (S), Threonine (T); 2) Aspartic acid (D), Glutamic acid (E); 3) Asparagine (N), Glutamine (Q); 4) Arginine (R), Lysine (K); 5) Isoleucine (I), Leucine (L), Methionine (M), Valine (V); and 6) Phenylalanine (F), Tyrosine (Y), Tryptophan (W).

A non-conservative amino acid substitution can result from changes in: (a) the structure of the amino acid backbone in the area of the substitution; (b) the charge or hydrophobicity of the amino acid; or (c) the bulk of an amino acid side chain. Substitutions generally expected to produce the greatest changes in protein properties are those in which: (a) a hydrophilic residue is substituted for (or by) a hydrophobic residue; (b) a proline is substituted for (or by) any other residue; (c) a residue having a bulky side chain, e.g., phenylalanine, is substituted for (or by) one not having a side chain, e.g., glycine; or (d) a residue having an electropositive side chain, e.g., lysyl, arginyl, or histadyl, is substituted for (or by) an electronegative residue, e.g., glutamyl or aspartyl. Variant amino acid sequences may, for example, be 80, 90 or even 95 or 98% identical to the native amino acid sequence. Programs and algorithms for determining percentage identity can be found at the NCBI website.

As used herein, the term "purified" does not require absolute purity; rather, it is intended as a relative term. Thus, for example, a purified protein preparation is one in which the protein referred to is more pure than the protein in its natural environment within a cell. For example, a preparation of a protein is purified such that the protein represents at least 50% of the total protein content of the preparation. Similarly, a purified oligonucleotide preparation is one in which the oligonucleotide is purer than in an environment including a complex mixture of oligonucleotides. Purity of a compound may be determined, for example, by high performance liquid chromatography (HPLC) or other conventional methods.

As used herein, "recombinant" generally refers to recombinant nucleic acid or protein that has a sequence that is not naturally occurring or has a sequence that is made by an artificial combination of two otherwise separated segments of sequence. This artificial combination is often accomplished by chemical synthesis or by the artificial manipulation of isolated segments of nucleic acids, for example, by genetic engineering techniques. The term recombinant includes nucleic acids and proteins that have been altered solely by addition, substitution, or deletion of a portion of a natural nucleic acid molecule or protein.

As used herein, the terms, "substantial identity" or "substantially identical" generally refer to a nucleic acid or fragment thereof, that, when optimally aligned with appropriate nucleotide insertions or deletions with another nucleic acid (or its complementary strand), refers to a nucleotide sequence having at least about 95% sequence identity, as measured by any well-known algorithm of sequence identity, such as FASTA, BLAST or Gap, as discussed below. A nucleic acid molecule having substantial identity to a reference nucleic acid molecule may, in certain instances, encode a polypeptide having the same or substantially similar amino acid sequence as the polypeptide encoded by the reference nucleic acid molecule.

As applied to polypeptides, the term "substantial similarity" or "substantially similar" means that two peptide sequences, when optimally aligned, such as by the programs GAP or BESTFIT using default gap weights, share at least 95% sequence identity, even more preferably at least 98% or 99% sequence identity. Preferably, residue positions which are not identical differ by conservative amino acid substitutions. A "conservative amino acid substitution" is one in which an amino acid residue is substituted by another amino acid residue having a side chain (R group) with similar chemical properties (e.g., charge or hydrophobicity). In general, a conservative amino acid substitution will not substantially change the functional properties of a protein. In cases where two or more amino acid sequences differ from each other by conservative substitutions, the percent sequence identity or degree of similarity may be adjusted upwards to correct for the conservative nature of the substitution. Means for making this adjustment are well-known to those of skill in the art. See, e.g., Pearson (1994) Methods Mol. Biol. 24: 307-331, herein incorporated by reference. Examples of groups of amino acids that have side chains with similar chemical properties include (1) aliphatic side chains: glycine, alanine, valine, leucine and isoleucine; (2) aliphatic-hydroxyl side chains: serine and threonine; (3) amide-containing side chains: asparagine and glutamine; (4) aromatic side chains: phenylalanine, tyrosine, and tryptophan; (5) basic side chains: lysine, arginine, and histidine; (6) acidic side chains: aspartate and glutamate, and (7) sulfur-containing side chains are cysteine and methionine. Preferred conservative amino acids substitution groups are: valine-leucine-isoleucine, phenylalanine-tyrosine, lysine-arginine, alanine-valine, glutamate-aspartate, and asparagine-glutamine. Alternatively, a conservative replacement is any change having a positive value in the PAM250 log-likelihood matrix disclosed in Gonnet et al. (1992) Science 256: 1443-1445, herein incorporated by reference. A "moderately conservative" replacement is any change having a nonnegative value in the PAM250 log-likelihood matrix.

Sequence similarity for polypeptides, which is also referred to as sequence identity, is typically measured using sequence analysis software. Protein analysis software matches similar sequences using measures of similarity assigned to various substitutions, deletions and other modifications, including conservative amino acid substitutions. For instance, GCG software contains programs such as Gap and Bestfit which can be used with default parameters to determine sequence homology or sequence identity between closely related polypeptides, such as homologous polypeptides from different species of organisms or between a wild type protein and a mutant thereof. See, e.g., GCG Version 6.1. Polypeptide sequences also can be compared using FASTA using default or recommended parameters, a program in GCG Version 6.1. FASTA (e.g., FASTA2 and FASTA3) provides alignments and percent sequence identity of the regions of the best overlap between the query and search sequences (Pearson (2000) supra). Another preferred algorithm when comparing a sequence of the invention to a database containing a large number of sequences from different organisms is the computer program BLAST, especially BLASTP or TBLASTN, using default parameters. See, e.g., Altschul et al. (1990) J. Mol. Biol. 215:403-410 and Altschul et al. (1997) Nucleic Acids Res. 25:3389-402, each herein incorporated by reference.

As used herein, "variant" generally refers to a peptide or polypeptide that differs in amino acid sequence by the insertion, deletion, or conservative substitution of amino acids, but retain at least one biological activity. "SNP" refers to a variant that is a single nucleotide polymorphism. Representative examples of "biological activity" include the ability to be bound by a specific antibody or to promote an immune response. Variant is also used herein to describe a protein with an amino acid sequence that is substantially identical to a referenced protein with an amino acid sequence that retains at least one biological activity. A conservative substitution of an amino acid, i.e., replacing an amino acid with a different amino acid of similar properties (e.g., hydrophilicity, degree, and distribution of charged regions) is recognized in the art as typically involving a minor change. These minor changes can be identified, in part, by considering the hydropathic index of amino acids, as understood in the art. Kyte et al., *J. Mol. Biol.* 157:105-132 (1982). The hydropathic index of an amino acid is based on a consideration of its hydrophobicity and charge. It is known in the art that amino acids of similar hydropathic indexes can be substituted and still retain protein function. In one aspect, amino acids having hydropathic indexes of ±2 are substituted. The hydrophilicity of amino acids can also be used to reveal substitutions that would result in proteins retaining biological function. A consideration of the hydrophilicity of amino acids in the context of a peptide permits calculation of the greatest local average hydrophilicity of that peptide, a useful measure that has been reported to correlate well with antigenicity and immunogenicity. Substitution of amino acids having similar hydrophilicity values can result in peptides retaining biological activity, for example immunogenicity, as is understood in the art. Substitutions may be performed with amino acids having hydrophilicity values within ±2 of each other. Both the hydrophobicity index and the hydrophilicity value of amino acids are influenced by the particular side chain of that amino acid. Consistent with that observation, amino acid substitutions that are compatible with biological function are understood to depend on the relative similarity of the amino acids, and particularly the side chains of those amino acids, as revealed by the hydrophobicity, hydrophilicity, charge, size, and other properties.

As used herein, "pause" generally refers to a section of a current stream in which the fluctuations in measured current are interrupted by a slower feature of about twice the duration of the neighboring features. Typically, a pause is observed before and after a nucleotide has been incorporated into a template sequence, and the duration of the pause relative to the neighboring pulses of current increases as the concentration of nucleotide triphosphates is lowered.

As used herein, a "polymerase" generally refers to an enzyme that synthesizes long chains of polymers or nucleic acids. DNA polymerase and RNA polymerase are used to assemble DNA and RNA molecules, respectively, by copying a DNA template strand using base-pairing interactions or RNA by half ladder replication.

Unless otherwise defined, all technical and scientific terms used herein have the same meaning as commonly understood by one of ordinary skill in the art. In case of conflict, the present document, including definitions, will control. Preferred methods and materials are described below, although methods and materials similar or equivalent to those described herein can be used in practice or testing of the present disclosure. All publications, patent applications, patents and other references mentioned herein are incorporated by reference in their entirety. The materials, methods, and examples disclosed herein are illustrative only and not intended to be limiting.

As noted herein, the disclosed embodiments have been presented for illustrative purposes only and are not limiting. Other embodiments are possible and are covered by the disclosure, which will be apparent from the teachings contained herein. Thus, the breadth and scope of the disclosure should not be limited by any of the above-described embodiments but should be defined only in accordance with claims supported by the present disclosure and their equivalents. Moreover, embodiments of the subject disclosure may include methods, compositions, systems and apparatuses/devices which may further include any and all elements from any other disclosed methods, compositions, systems, and devices, including any and all elements corresponding to detecting protein activity. In other words, elements from one or another disclosed embodiments may be interchangeable with elements from other disclosed embodiments. Moreover, some further embodiments may be realized by combining one and/or another feature disclosed herein with methods, compositions, systems and devices, and one or more features thereof, disclosed in materials incorporated by reference. In addition, one or more features/elements of disclosed embodiments may be removed and still result in patentable subject matter (and thus, resulting in yet more embodiments of the subject disclosure). Furthermore, some embodiments correspond to methods, compositions, systems, and devices which specifically lack one and/or another element, structure, and/or steps (as applicable), as compared to teachings of the prior art, and therefore represent patentable subject matter and are distinguishable therefrom (i.e., claims directed to such embodiments may contain negative limitations to note the lack of one or more features prior art teachings).

2. Bioelectronic Devices and Systems

As molecular electronic components, proteins are distinguished by a remarkably long electronic decay length (~10 nm) together with high contact resistance and extreme sensitivity to the chemical details of the contact. As a consequence, the conductance of even a large bioelectronic assembly is largely controlled by the conductance of the contacts. For example, streptavidin is a versatile linker-protein that can tether together biotinylated electrodes and biotinylated proteins, but with an ambiguity about the contact geometry that arises from its four possible binding sites for biotin. That is, the distribution of measured conductances for streptavidin molecules (and complexes connected via streptavidin) has multiple peaks, indicative of multiple modes of connection, made possible by the tetravalent nature of streptavidin. This ambiguity in connection geometries is not easily resolved.

Breaking the protein into subunits can produce a dimeric streptavidin, but only at the cost of a large decrease in biotin binding strength because the interaction is largely driven by cooperative interactions in the hydration shell of the tetramer. Previous studies have introduced an ingenious method for synthesizing tetramers of defined valence with no diminution in biotin binding affinity. These studies used engineered monomers (SAe) with wild-type sequences, but labeled with hexaglutamate tails at the C terminus. Previous studies have also engineered dead units (D) containing the mutations N32A, S27D and S45A that did not bind biotin. They then refolded mixtures of SAe and D monomers, and used ion-exchange chromatography to select molecules with the desired ratio of SAe to D units. (These combinations are shown schematically in FIG. 1C.) The SAe2D2 molecule labeled 1,3 carries a slightly higher charge density than the other divalent combinations (1,2 and 1,4) and can therefore be separated from them. As described further herein, conductance distributions were measured for these modified streptavidins and used to connect doubly-biotinylated Φ29 to electrodes. In addition to clarifying the role of streptavidin contacts, these experiments demonstrate how a multi-protein complex has a conductance little different than the conductance of the units used to make the contacts, and also show how engineering the interfacial charge can modulate molecular conductance.

In accordance with the above, embodiments of the present disclosure use engineered streptavidin tetramers, selected to contain a defined ratio of active monomers to "dead" monomers so as to define the biotin binding sites. As described further herein, a strong dependence of conductance on the separation of the biotin molecules was found, consistent with a short-range tunneling interaction, and in contrast to the long-range transport observed inside larger proteins. In some embodiments, hexaglutamate tails label the active monomers and the additional negative charge enhances conductance significantly. This effect is quantitatively accounted for by an electronic resonance in the protein conductance.

Modified Streptavidin Tetramers. Exemplary embodiments of the various modular arrangements of streptavidin monomers are described herein. For example, FIG. 1A shows the arrangement of the four bound biotins in a tetravalent streptavidin tetramer (RSC PDB 1STP). Labeled distances are measured between the sulfur atoms of the four biotins. The arrows show the directions of the tails of the biotin ligands used to form the crystal (the thiolated biotin used as an electrical connecter in the present disclosure is shown). FIG. 1B shows the backbone structure of the tetramer in the same orientation as the ligands in FIG. 1A. Hexaglutamate tails ($E_6$) are shown schematically on the four C termini (note that the crystal structure is truncated at residue 133, so residues 134-159 are missing here). The four monomers are labeled 1-4 to correspond to the four ligands in FIG. 1A. The hexaglutamate tail is oriented approximately normal to the biotin binding tails, and schematic representations of the arrangements of the reconstituted tetramers are shown in FIG. 1C, where the black arrows represent the biotin tails and the red lines the hexaglutamate tags. Each of these tetramers is separable on an ion exchange column, with the exception of the 1,2 and 1,4 SAe2D2 tetramers which were prepared as a mixture.

Figure 5:
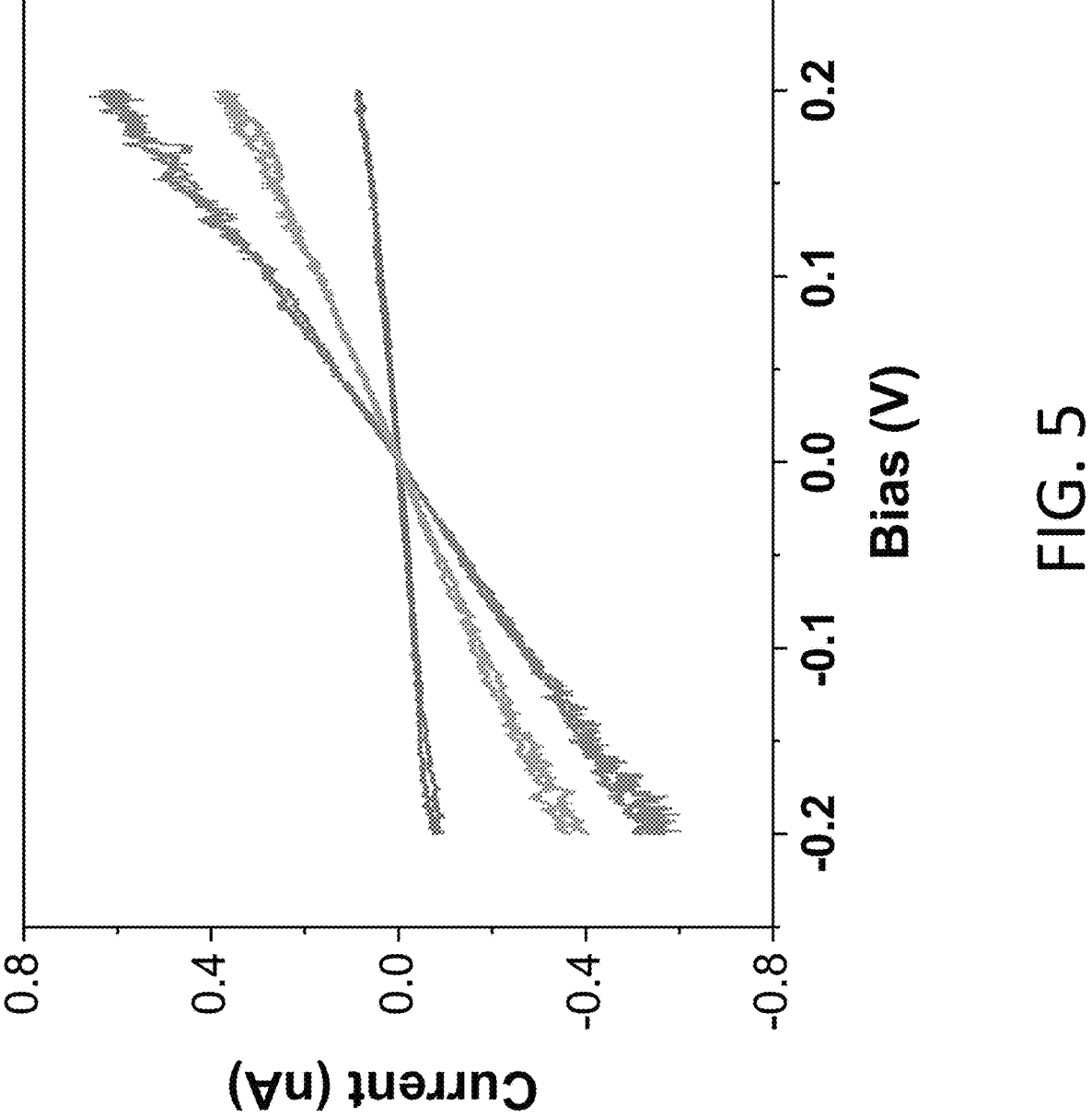
FIG. 5: Representative samples of current-voltage (IV) characteristics for SAe4. Each color corresponds to data obtained from a different molecule.

Conductance Measurements. Electrochemical scanning tunneling microscopy (STM) was used to record the conductances of this series of streptavidin tetramers. The gap was set to a fixed set point conductance (4 pA at 0.2 V, corresponding to a distance $Z_0$ of approximately 2.5 nm[10]), and the probe then retracted by a fixed number of nm, waiting for a jump in current signaling that a protein has been caught between probe and substrate, and then recording up to 60 current-vs.-voltage curves in the minute for which the gap remained stable without servo control. For streptavidin alone, measurements were made at the set-point gap, $Z_0$. There were essentially no contacts recorded at $Z_0+1$ nm. For complexes bridged with polymerases, gaps were set to $Z_0+2$ nm. Pd substrates and polyethylene-coated Pd probes were used, both of which were functionalized with the thiolated biotin molecule in FIG. 1A. The potential of the substrate was set to 0 V with respect to a salt-bridged Ag/AgCl reference electrode. Current-voltage curves were linear and reproducible on changing sweep direction for the SAe4 configuration (see, e.g., FIG. 5; each curve is from a different molecule of the SAe4). The slope of each curve yields a conductance for a particular molecule in a given contact geometry, and conductance histograms are compiled for many molecules of a given composition in FIG. 2. Data for the SAe/D combinations are shown in FIGS. 2A-2E, and data for the WT streptavidin are shown in FIG. 2F.

Figures 2A, 2B, 2C, 2D, 2E, 2F:
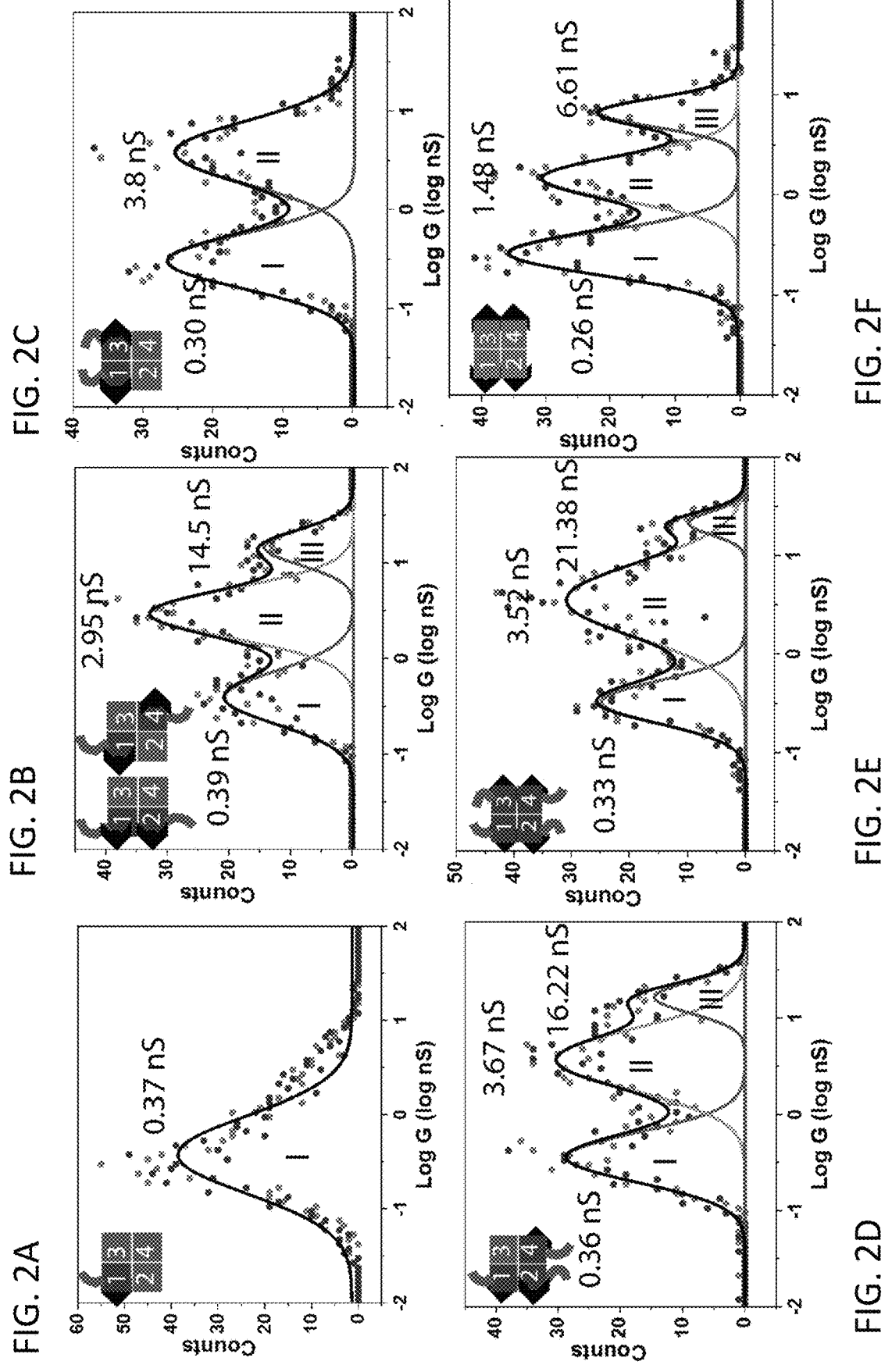
FIGS. 2A-2F: Measured distributions of conductance for SAe1D1 (FIG. 2A); SAe2D2 1,2 and 1,4 mixture (FIG. 2B); SAe2D2 1,3 (FIG. 2C); SAe3D1 (FIG. 2D); SAe4 (FIG. 2E); and wild type streptavidin (FIG. 2F).

The SAe1D3 distribution (FIG. 2A) shows one peak at about 0.3 nS, similar to results for other singly-connected proteins, so it was reasoned that the peaks labeled I in the remaining FIGS. 2B-2F result from singly connected molecules. The distribution for the SAe2D2 molecule in the 1,3 trans configuration (FIG. 2C) has two peaks, so the additional peak labeled II arises from doubly-connected molecules. The 1,2 and 1,4 mixture of SAe2D2 molecules has an additional peak (III). Since the distance between the biotin ligands is smaller for the 1,4 connection, it was tentatively assigned peak III to a 1,4 bridge and peak II to a 1,2 bridge. The SAe3D1 molecule has a distribution (FIG. 2D) that is similar to the 1,2 and 1,4 mixture suggesting that peak II is a 1,2 connection and peak III is a 1,4 connection. The distribution for the SAe4 (FIG. 2E) is again similar to that for the 1,2 and 1,4 mixtures and the SAe3D1 mutant. In this case, the 1,2 and 3,4 connections and the 1,4 and 3,2 connections have equivalent geometries, so the bonding possibilities give rise to a distribution that mirrors that for the 1,4 and 1,2 mixture (FIG. 2B). There is an additional possibility, which is that the molecules with 3 or 4 valencies could form additional contacts with the biotin-functionalized substrate, leading to additional peaks in the distribution, but these are not observed, presumably because of the steric constraints imposed by binding of the biotins to the metal electrodes.

One surprising and unexpected feature of the distributions is the large value of the highest conduction peak for the mutant streptavidins (FIGS. 2B, 2D, and 2E) compared to the highest peak (III) for the WT (with the exception of the SAe2D2 1,3 trans connection that lacks peak III). This is surprising because the only difference between SAe4 and the WT is the presence of the hexaglutamate chains. These are remote from the biotin binding sites and therefore might not be expected to influence conductance. However, it was shown earlier that protein conductance is strongly dependent on electron energy as controlled by altering the surface potential (either by using different metals for the electrodes or operating under electrochemical potential control). To test this mechanism, the rest potential of Pd electrodes functionalized with thio-biotin and a monolayer of the various streptavidin molecules was measured. The results are summarized in Table 1.

TABLE 1

Rest potential and peak conductance values for the streptavidin molecules.

| Molecule | Rest Potential (mv vs. NHE) | Conductance Peak I (nS) | Conductance Peak II (nS) | Conductance Peak III (nS) |
|---|---|---|---|---|
| SAe4 | 330.2 ± 1.9 | 0.33 ± 0.02 | 3.52 ± 0.16 | 21.38 ± 1.48 |
| SAe3D1 | 351.7 ± 1.7 | 0.36 ± 0.01 | 3.67 ± 0.17 | 16.22 ± 1.12 |
| SAe2D2 1,3 | 398.9 ± 0.7 | 0.30 ± 0.01 | 3.80 ± 0.09 | NA |
| SAe2D2 1,2 1,4 | 383.4 ± 0.9 | 0.39 ± 0.02 | 2.95 ± 0.07 | 14.45 ± 0.67 |
| SAe1D3 | 410.0 ± 0.4 | 0.37 ± 0.01 | NA | NA |
| WT | 458.3 ± 1.6 | 0.26 ± 0.01 | 1.48 ± 0.03 | 6.61 ± 0.19 |

Figure 3:
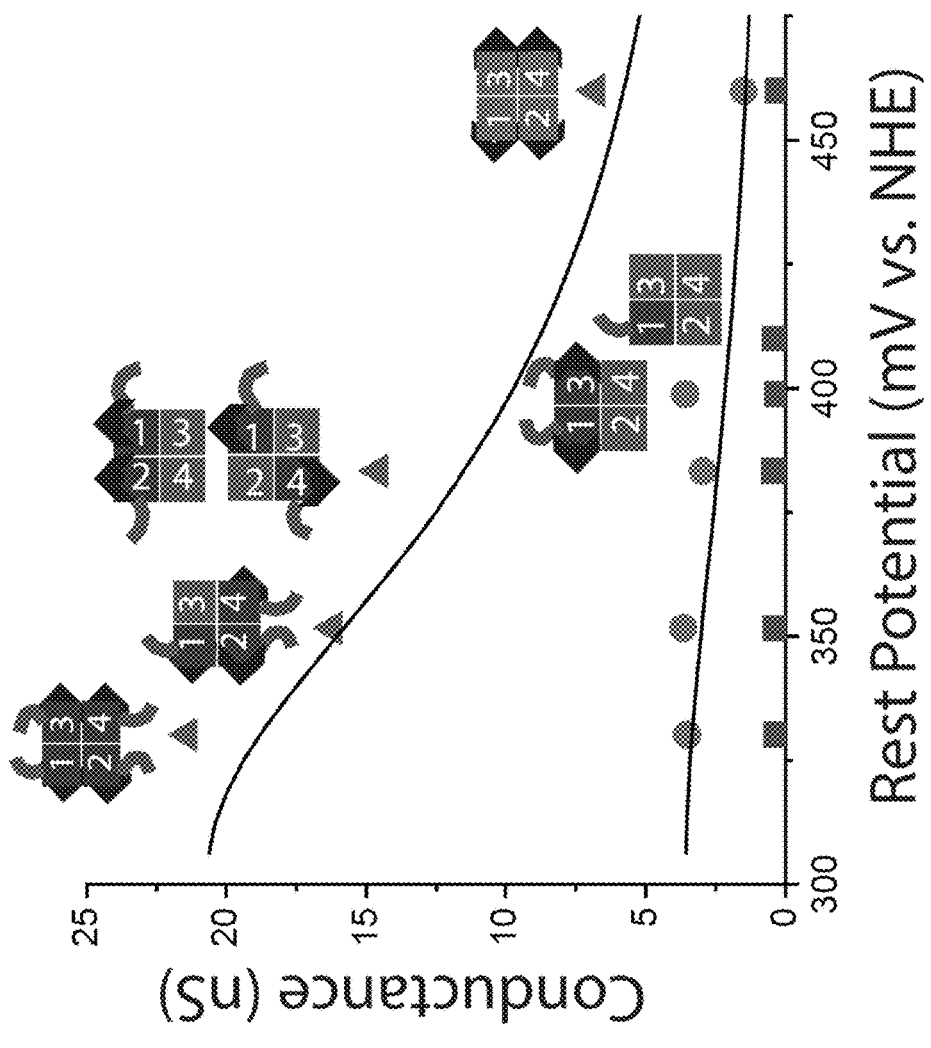
FIG. 3: Conductance of the various tetramer compositions as a function of measured surface potential for Peak III (blue triangles), Peak II (red dots), and Peak 1 (black squares). The lines are the Lorentzian curves fitted to data for WT streptavidin taken as a function of potential.

These conductances are plotted vs. measured rest potential for the various molecules in FIG. 3. The curves are the Lorentzian fits to the measured conductances for WT streptavidin as a function of surface potential for peaks II and III. Clearly the measured change in surface potential and the corresponding shift in electron injection energy relative to the resonance peak accounts for the effects of the hexaglutamate tails, showing how electrode metals far from the intrinsic resonance can be modified by surface charge on the attached proteins.

Figure 6B:
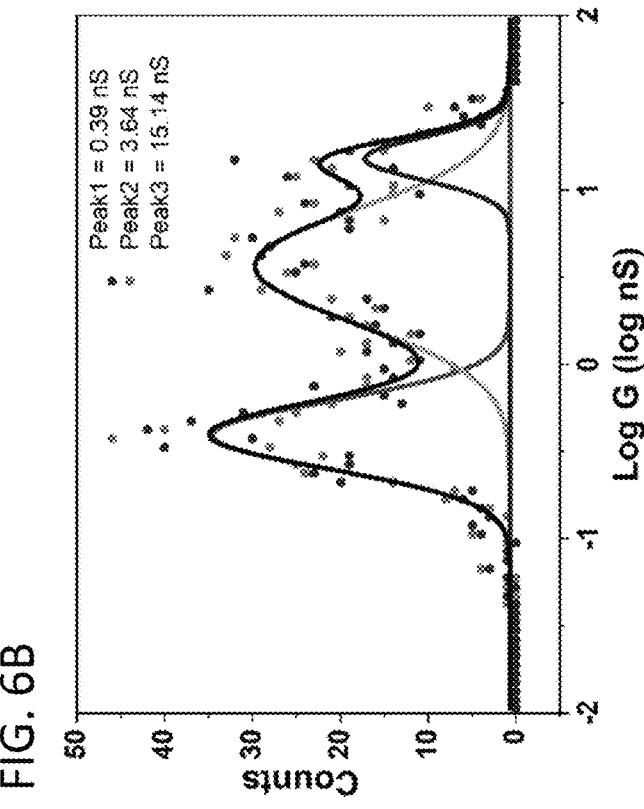
FIGS. 6A-6B: Conductance distribution for the Φ29 connected by SAe4 in the presence of primer, template and $Mg^{2+}$ (FIG. 6A), and with the addition of dNTPs (FIG. 6B). The third peak (highest conductance, fitted by the blue line) in the distribution corresponds to the desired two specific connections to the polymerase via streptavidin molecules. In the absence of dNTPs, the conductance of the third peak is 11.2 nS. When dNTPs are added, the conductance increases to 15.1 nS. These conductances are higher than obtained with wild-type streptavidin connections (6 nS in the absence of dNTPs and 12 nS when dNTPs are added).
Figure 6A:
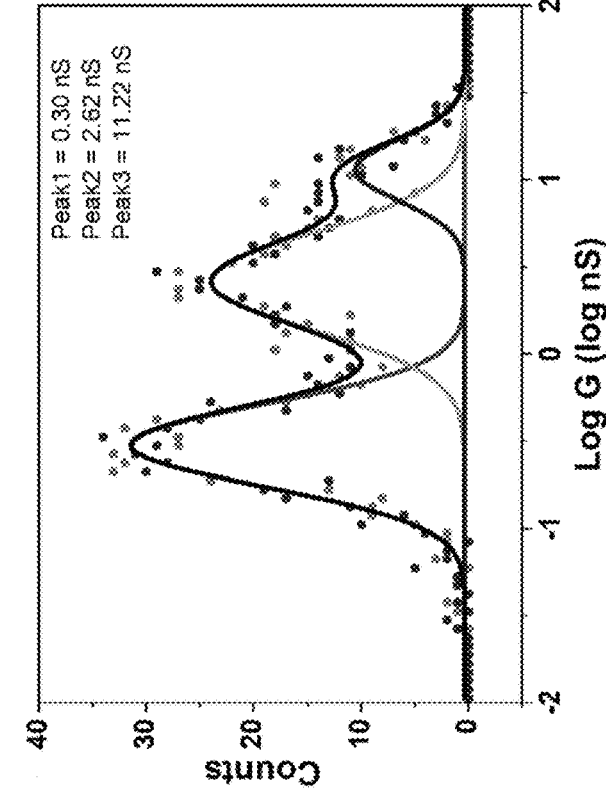
Figure 7:
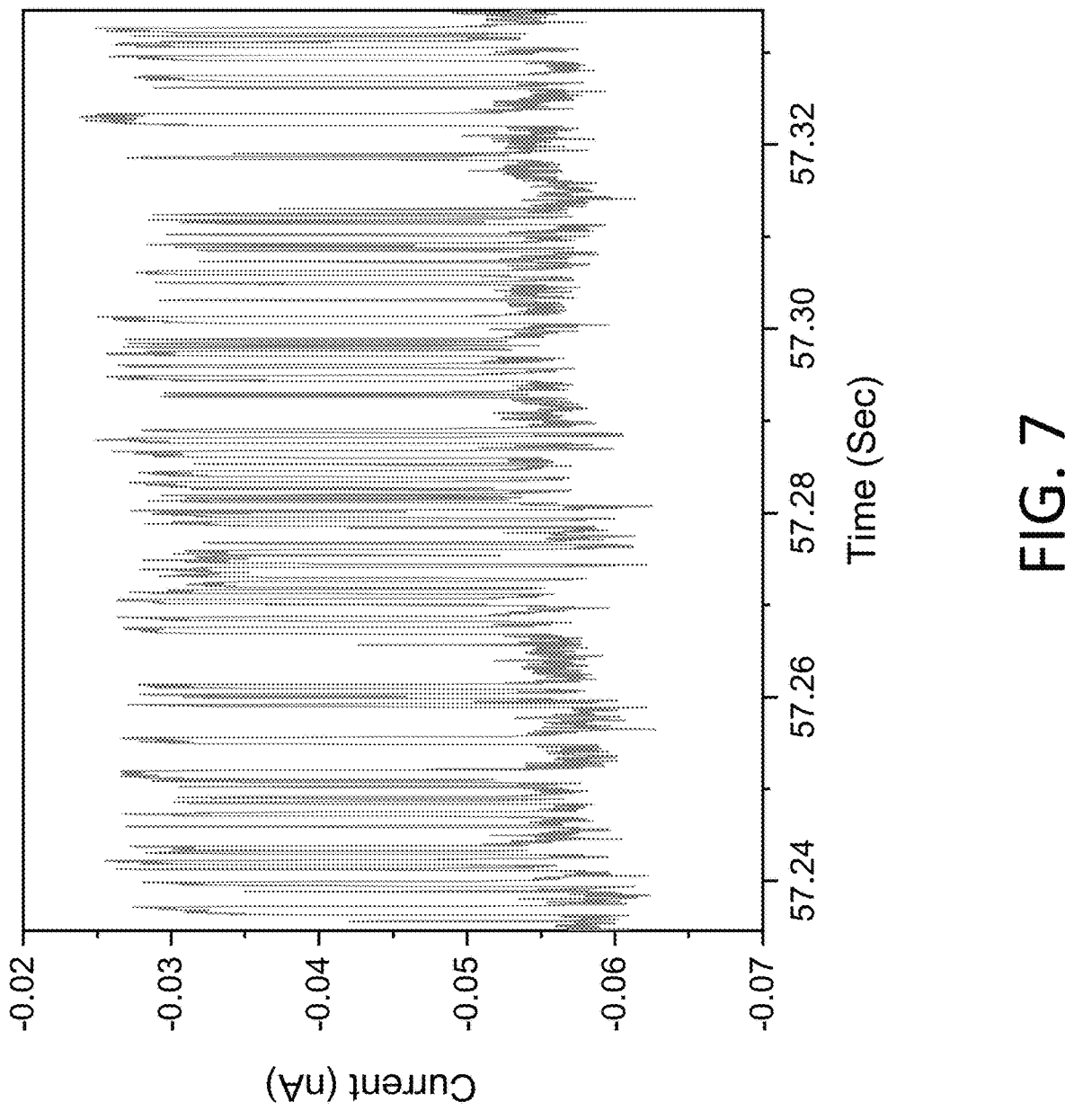
FIG. 7: Current fluctuations observed after the induction of Φ29 activity on addition of 1 mM dNTPs. These measurements are taken by holding the bias constant at 50 mV and recording the current as a function of time. Prior to the addition of dNTPs, the current is constant (to within the background noise of ~10 pA). After the addition of dNTPs, the current becomes –60 pA (increasing negative current is downwards in this plot), with sharp spikes to a reduced current of 30 pA corresponding to the closed state of the polymerase.

An important goal of the present disclosure is to better understand the role of streptavidin as a molecular wire and programmable connector in bioelectronic circuits (the focus being the incorporation of a DNA polymerase into a bio-electronic circuit). The circuit is shown schematically in FIG. 4A where wild type streptavidin (green) connects a doubly-biotinylated Φ29 polymerase to biotinylated electrodes. The conductance distribution measured at a 4.5 nm gap is shown, with three conductance peaks (0.26, 1.47 and 6.61 nS). No conductance is observed at all at this gap when the electrodes are coated with streptavidin but no polymerase is present. Furthermore, the distributions are sensitive to the addition of dNTPs to polymerases with primed templates, and large-amplitude telegraph noise is observed when the polymerase is activated (see, e.g., FIGS. 6 and 7) showing that the current path is through the polymerase. Based on the distributions shown in FIG. 2, the 0.26 nS peak I in for the WT connectors (FIG. 4A) corresponds to one specific contact via a bound biotin and a second, non-specific contact to some other point on the complex. Presumably, the high conductance peak (6.61 nS) reflects the formation of complexes connected by specific biotin-streptavidin binding at each of the electrodes. The origin of the middle peak (1.47 nS) may reflect a second type of bonding geometry for the tetravalent WT streptavidin.

Figures 4A, 4B, 4C:
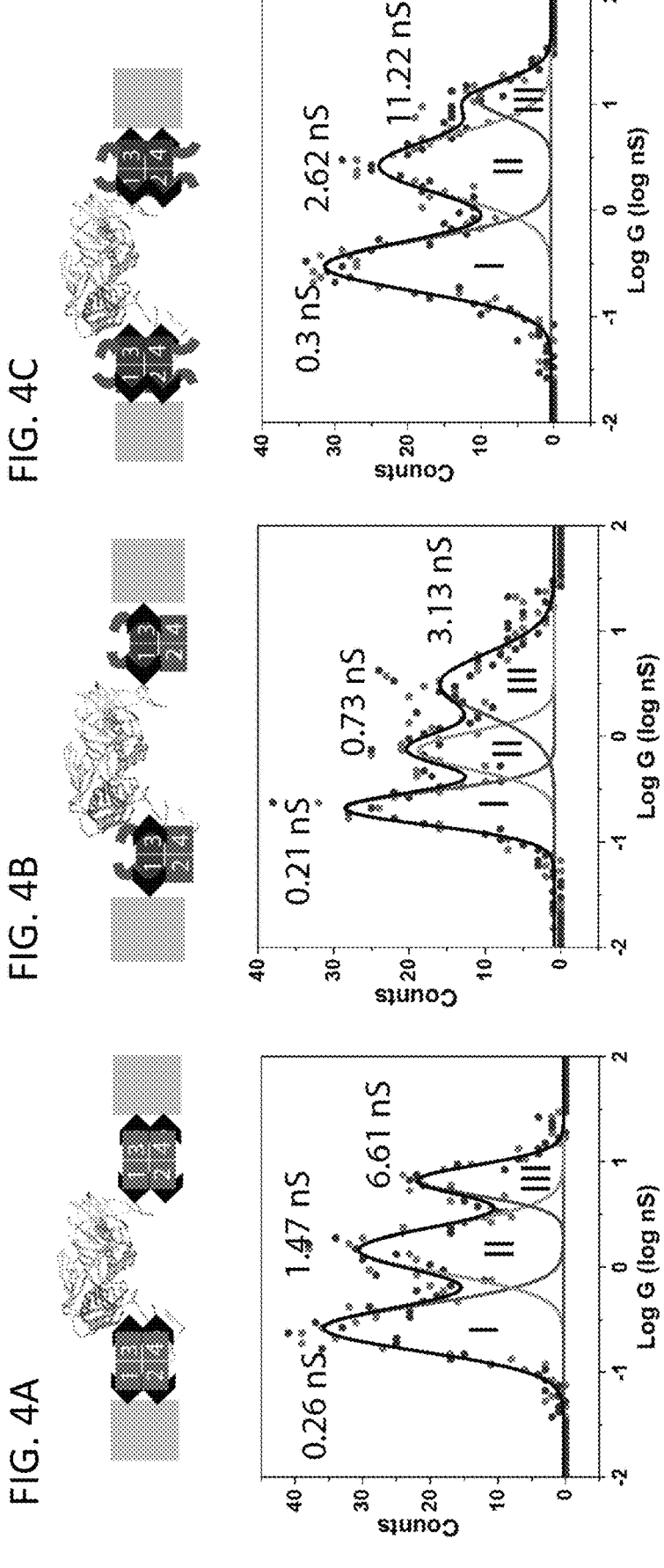
FIGS. 4A-4C: Conductance distributions measured for streptavidin functionalized electrodes bridged by a doubly-biotinylated Φ29 polymerase with WT streptavidin (FIG. 4A), the SAe2D2 1,3 tetramer (FIG. 4B), and the SAe4 tetramer (FIG. 4C).

FIG. 4B shows the distribution measured with the SAe2D2 1,3 molecule. Three peaks are also observed with this molecule with only one doubly-bonded geometry available, which therefore eliminates the possibility that the middle peak comes from some alternate streptavidin binding. It must be a feature associated with the presence of the polymerase in the gap. Comparing the distributions in FIG. 2F (WT SA alone in a 2.5 nm gap) and FIG. 4A (WT SF bridged by Φ29 in a 4.5 nm gap) shows that the conductance peaks are essentially identical in the two cases, emphasizing the point that the conductance of a complex is dictated almost entirely by the limiting conductance of the contacts. The SAe2D2 1,3 molecule alone (FIG. 2C) has about half the conductance of the WT (FIG. 2F) for the largest peak. Correspondingly, the peak conductance in the distribution for Φ29 contacted by SAe2D2 1,3 (FIG. 4B) is about half that of the polymerase contacted by WT streptavidins. The same effect is observed for Φ29 contacted by SAe4 (FIG. 4C) where the highest conductance (peak III) is about double that of the complex connected by WT streptavidin, reflecting the increased conductance of the SAe4 alone (FIG. 2E). The fact that the additional biotin binding sites in the WT and SAe4 do not lead to additional features in the conductance distributions when compared to the distribution for the SAe2D2 1,3 (FIG. 4B) suggests that steric constraints in binding the bridging Φ29 limit the number of likely binding geometries.

That the contact conductance dominates the overall conductance in these much larger assemblies is likely a consequence of the very slow decay of conductance with distance in the interior of the proteins measured to date, coupled with the large charge injection barrier presented by the hydrated protein exterior. The charge transfer process that underlies these very long decay lengths likely does not apply in the region of the contacts because of the sensitivity to local chemical geometry. If the difference between the conductance of the 1,4 and 1,3 contacts is a consequence of the different distances separating the ligands in the two cases (FIG. 1A), it suggests that the electronic decay length within the streptavidin is small. Specifically, the conductance changes from 14.5 nS to 3.8 nS as the interaction distance is increased from 2.13 to 2.53 nm. Assuming a dependence of the form $G=G_oexp$ $(-\beta z)$ leads to $\beta=3.4$ $nm^{-1}$, or a decay length of 0.3 nm. This much smaller length accords with known tunneling distances in proteins and is also characteristic of the measured decay in small, hydrated peptides. Strepavidin's small size and its solvent accessible ligand binding pockets may prevent the development of the states responsible for long-range conductance in larger proteins.

Taken together, the results of the present disclosure demonstrate that small changes in the contact chemistry dominate the overall conductance of even large inter-connected complexes and indicate that the electronic interaction length in the contact region is small (ca. 0.3 nm). While some of the binding modes of streptavidin have been identified (for example, the SAe2D2 1,3 offers only one possible bridging geometry) other features, such as the middle peak in the Φ29 distributions, remain unaccounted for. These results also demonstrate how modification of the electrode surface potential via charged residues on the protein contacts strongly modulates overall conductance, an effect quantitatively accounted for by the observed electronic resonance in conductance. This may be an important result for practical devices made using CMOS processes, where gold cannot be used. Metals with a much more positive surface potential will yield lower signals with given connection chemistry, but this loss might be readily offset by incorporating negatively charged residues in the contact region.

Additionally, certain effects on contact geometry were also observed. For example, in addition to the enhancement of conductance that is obtained from the addition of charged residues (e.g., FIG. 3), there is a significant difference that arises from the arrangement of the live and dead monomers within the tetramer as is evident by comparing FIGS. 2B and 2C. Each of these tetramers contains two monomers with hexaglutamate tails. However, the SAe2D2 1,2 1,4 molecules have significantly higher conductance (FIG. 2B) than the SAe2D2 1,3 molecule (FIG. 2C).

Thus, embodiments of the present disclosure make use of the above novel findings to generate bioelectronic devices and systems that modulate electrical conductance through a protein-of-interest to obtain a bioelectronic signature of protein activity. Thus, the present disclosure provides bioelectronic devices and systems comprising a first electrode and a second electrode separated by a gap. In some embodiments, the first and/or the second electrode comprises gold, palladium, platinum, silver, copper, or any alloys thereof. The various features or characteristics of a bioelectronic signature of an active protein-of-interest can be used, for example, to determine the sequence of a biopolymer. As would be recognized by one of skill in the art based on the present disclosure, the methods of obtaining a bioelectronic signature and extracting various characteristics described herein can be used to determine the sequence of any biopolymer using any corresponding enzyme-of-interest, including but not limited to a polymerase, a nuclease, a proteasome, a glycopeptidase, a glycosidase, a kinase and an endonuclease.

In accordance with these embodiments, the bioelectronic devices and systems further comprises a protein-of-interest attached to the first and second electrodes via a linker. In some embodiments, the linker includes an assembly of monomers comprising at least one ligand-binding monomer and at least one non-ligand-binding monomer. In some embodiments, the assembly of monomers are configured to maximize electronic conductance through the protein-of-interest. However, as described further herein, in some embodiments, the assembly of monomers can be configured to modulate electronic conductance through the protein-of-interest such that a desired amount of electronic conductance is achieved (see, e.g., FIGS. 4A-4C).

In some embodiments, the bioelectronic devices and systems of the present disclosure include a linker comprising two ligand-binding monomers. In some embodiments, the bioelectronic devices and systems of the present disclosure include a linker comprising three ligand-binding monomers. In other embodiments, the bioelectronic devices and systems of the present disclosure include a linker comprising two non-ligand-binding monomers (FIG. 1). In accordance with these embodiments, the assembly of monomers comprises two ligand-binding monomers arranged in trans (FIG. 1C). In some embodiments, the assembly of monomers comprises two ligand-binding monomers arranged in cis (FIG. 1C). In some embodiments, the assembly of monomers comprises three ligand-binding monomers and exhibits a higher conductance compared to an assembly of monomers comprising two ligand-binding monomers (FIG. 3).

In some embodiments, the linker comprises a peptide or polypeptide. In some embodiments, the linker comprises streptavidin, or a functional derivative or variant thereof. In some embodiments, the linker further comprises a tag. In some embodiments, the tag comprises a negative charge. In some embodiments, the tag comprises at least one of a glutamate moiety and/or an aspartate moiety. In some embodiments, the tag comprises at least two glutamate moieties. In some embodiments, the tag comprises a hexa-glutamate moiety. In some embodiments, the tag is coupled to the C-terminal end of each of the at least one ligand-binding monomers in the assembly.

In some embodiments, the linker comprises streptavidin that has been modified to have a positive or negative charge (e.g., with polyglutamate). In some embodiments, the protein-of-interest is biotinylated. In some embodiments, the linker comprises a distinctive negative charge. In some embodiments, the distinctive negative charge is conferred by addition of a glutamate moiety, an aspartate moiety, or a combination thereof (including derivatives, variants, and polymers), coupled to the streptavidin. In some embodiments, the distinctive negative charge increases the conductance through the protein. In some embodiments, the linker comprises a distinctive positive charge. In some embodiments, the distinctive positive charge is conferred by addition of an arginine moiety, a histidine moiety, a lysine moiety, or a combination thereof (including derivatives, variants, and polymers), coupled to the streptavidin. In some embodiments, the distinctive positive charge increases or decreases the conductance through the protein.

In some embodiments, the bioelectronic devices and systems of the present disclosure include a protein attached to the first and second electrodes (e.g., via a linker). In some embodiments, the protein is a polymerase, and it is attached to one electrode in one embodiment or to both electrodes in another embodiment. The polymerase can be attached to the electrode(s) either directly or indirectly. In some embodiments, the polymerase is attached to the electrode(s) via a linker. In some embodiments, the polymerase is attached to the electrode indirectly via interactions with a ligand attached to the electrode. In some embodiments, the polymerase is modified to incorporate a ligand and/or a ligand-binding site. In some embodiments, the polymerase is a biotinylated polymerase (e.g., the ligand is biotin). In some embodiments, the polymerase comprises an Avitag. In some embodiments, the polymerase is a biotinylated polymerase and is attached to the electrode via a linker comprising streptavidin (e.g., ligand-binding and non-ligand-binding monomers). In some embodiments, the polymerase is modified to incorporate an amino acid residue that allows for click-chemistry attachment of other chemical groups to the electrodes (e.g., 4-Azido-L-phenylalanine). In some embodiments, the exonuclease activity of the polymerase is disabled. In some embodiments, linker is attached to a region of the polymerase that is inactive.

Embodiments of the present disclosure also include a method of modulating electronic conductance through a protein using any of the devices described herein. In some embodiments, modulating electronic conductance comprises increasing conductance using the assembly of monomers comprising at least one ligand-binding monomer and at least one non-ligand-binding monomer as compared to using an assembly of monomers that does not comprise at least one ligand-binding monomer and at least one non-ligand-binding monomer.

Embodiments of the present disclosure also include a method for sequencing a polynucleotide using a bioelectronic device or system described herein. In accordance with these embodiments, the method includes (a) introducing a template polynucleotide to a bioelectronic device, wherein the bioelectronic device comprises a polymerase functionally coupled to at least one of a first electrode and a second electrode via a linker, wherein the linker comprises an assembly of monomers comprising at least one ligand-binding monomer and at least one non-ligand-binding monomer; (b) introducing a solution comprising four nucleotidepolyphosphate monomers to the device comprising the template polynucleotide; and (c) obtaining a bioelectronic signature of polymerase activity based on current fluctuations as each complementary nucleotidepolyphosphate monomer is incorporated into the template polynucleotide. In some embodiments, at least one characteristic of the bioelectronic signature identifies each of the complementary nucleotidepolyphosphate monomers incorporated into the template polynucleotide.

As one of ordinary skill in the art will readily recognize and appreciate after having benefited from the teachings of the present disclosure, the methods described herein can be used with any bioelectronic device that senses the duration of the open and closed states of an enzyme (e.g., polymerase). Exemplary devices include, but are not limited to, the bioelectronic devices and systems disclosed in U.S. Pat. No. 10,422,787 and PCT Appln. No. PCT/US2019/032707, both of which are herein incorporated by reference in their entirety and for all purposes. Additionally, it will be readily recognized and appreciated by those of ordinary skill in the art based on the present disclosure that the forgoing embodiments apply equally to (and include) sequencing RNAs with the substitution of rNTPs for dNTPs and the use of an RNA polymerase.

Further, one of ordinary skill in the art would readily recognize and appreciate that the methods described herein can be used in conjunction with other methods involving the sequencing of a biopolymer. In particular, the various embodiments disclosed in PCT Application No. PCT/US21/19428, which is herein incorporated by reference in its entirety, describes the interpretation of current fluctuations generated by a DNA polymerase as it actively extends a template, and how signal features (e.g., bioelectronic signature) may be interpreted in terms of the nucleotide being incorporated, and thus, how these signals can read the sequence of the template. This approach utilizes features of the signal that vary in time. For example, the time that the polymerase stays in a low current state reflects the concentration of the nucleotidetriphosphate in solution. If the concentration of a particular nucleotide triphosphate is low, then the polymerase must stay open for a longer time in order to capture the correct nucleotide, and since the open conformation of the polymerase corresponds to a lower current, the dip in current associated with the open state lasts for longer. Additionally, the various embodiments disclosed in PCT Application No. PCT/US20/38740, which is herein incorporated by reference in its entirety, describes how the base-stacking polymerization rate constant differences are reflected in the closed-state (high current states) so that the duration of these states may also be used as an indication of which one of the four nucleotides is being incorporated. It can be desirable to be able to use the amplitude of the signal as yet an additional contribution to determining sequence. Further, the various embodiments disclosed in PCT Application No. PCT/US21/17583, which is herein incorporated by reference in its entirety, describes methods that utilize a defined electrical potential to maximize electrical conductance of a protein-of-interest (e.g., polymerase), which can serve as a basis for the fabrication of enhanced bioelectronic devices for the direct measurement of protein activity.

3. Methods for Sequencing a Biopolymer

In accordance with the above methods, the bioelectronic devices and systems of the present disclosure generally include a first electrode and a second electrode separated by a gap. In some embodiments, the bioelectronic devices are configured for contact with a sample (e.g., biopolymer sample) to be analyzed. In some embodiments, such as when the electrodes are planar, the first and/or second electrode do not require a dielectric layer. In other embodiments, the first and/or second electrode can have a dielectric layer. In some embodiments, the first and/or second electrode comprise a metal selected from gold, silver, copper, platinum, palladium, and ruthenium (or any alloys thereof). In some embodiments, the metal is palladium.

In some embodiments, the methods of the present disclosure include applying a voltage bias between the first and second electrodes that is 100 mV or less. It will be recognized by one of ordinary skill in the art based on the present disclosure that the bioelectronic devices and systems of the present disclosure, according to the various methods described herein, can be used to sequence DNA and RNA polymers by similar techniques (e.g., sequence RNA polymers using an RNA dependent RNA polymerase and four different ribonucleotides each carrying a distinctive charge).

In some embodiments, the gap between the first and second electrode is a width of about 1.0 nm to about 50.0 nm. In some embodiments, the gap between the first and second electrode is a width of about 1.0 nm to about 40.0 nm. In some embodiments, the gap between the first and second electrode is a width of about 1.0 nm to about 30.0 nm. In some embodiments, the gap between the first and second electrode is a width of about 1.0 nm to about 20.0 nm. In some embodiments, the gap has a width of about 1.0 nm to about 10.0 nm. In some embodiments, the gap has a width of about 1.0 nm to about 7.5 nm. In some embodiments, the gap has a width of about 1.0 nm to about 5.0 nm. In some embodiments, the gap has a width of about 4.0 nm to about 5.0 nm.

In some embodiments, the bioelectronic devices and systems of the present disclosure include a protein attached to the first and second electrodes (e.g., via a linker). In some embodiments, the protein is selected from the group consisting of a polymerase, a nuclease, a proteasome, a glycopeptidase, a glycosidase, a kinase and an endonuclease. In some embodiments, the protein is a polymerase, and it is attached to one electrode in one embodiment or to both electrodes in another embodiment. The polymerase can be attached to the electrode(s) either directly or indirectly. In some embodiments, the polymerase is attached to the electrode(s) via a linker. In some embodiments, the polymerase is attached to the electrode indirectly via interactions with a ligand attached to the electrode. In some embodiments, the polymerase is modified to incorporate a ligand and/or a ligand-binding site. In some embodiments, the polymerase is a biotinylated polymerase (e.g., the ligand is biotin). In some embodiments, the polymerase comprises an Avitag. In some embodiments, the polymerase is a biotinylated polymerase and is attached to the electrode via a linker comprising streptavidin (e.g., ligand-binding and non-ligand-binding monomers). In some embodiments, the polymerase is modified to incorporate an amino acid residue that allows for click-chemistry attachment of other chemical groups to the electrodes (e.g., 4-Azido-L-phenylalanine). In some embodiments, the exonuclease activity of the polymerase is disabled. In some embodiments, linker is attached to a region of the polymerase that is inactive.

When the polymerase is attached to both electrodes, the distance between the two attachment points can be at least about 1 nm to about the overall size of the polymerase. In one embodiment, the distance is from about 1 nm to about 10 nm. In another embodiment, the distance is from about 3 nm to about 7 nm. In another embodiment, the distance is from about 5 nm to about 6 nm. In some embodiments, the distance is from about 2 to about 8 nm.

When the polymerase is attached to both electrodes, the two attachment points can be configured such that they do not move relative to each other, for example, when the polymerase undergoes open-to-closed conformational changes (e.g., while incorporating a nucleotide). The crystal structures of many polymerases are currently available (see, e.g., rcsb.org) in both open and closed forms. Thus, when choosing the two attachment points, the two residues can be separated from each other by distances that are similar to the gap between the electrodes used to contact the polymerase, such as between about 1 nm and about 10 nm. For example, in some embodiments, this distance is between 2 nm and 8 nm. In embodiments, the two attachment points have the same atomic coordinates in both the open and closed forms, to within half a nanometer.

In some embodiments, the bioelectronic devices and systems of the present disclosure include a nucleic acid template. The nucleic acid template can be a DNA template in one embodiment and an RNA template in another embodiment. In some embodiments, such as when a polymerase operates at maximum speed, and for the electrical signals to be readily processed, it is understood that the polymerase not be stalled or obstructed by secondary structures formed by the DNA template, such as when the template contains single stranded regions.

In some embodiments, the bioelectronic devices and systems of the present disclosure can be used to obtain a bioelectronic signature of polymerase activity based on current fluctuations as each complementary nucleotidepolyphosphate monomer is incorporated into the template polynucleotide. The various features or characteristics of a bioelectronic signature of an active protein-of-interest (e.g., a polymerase) can be used to determine the sequence of a biopolymer (e.g., polynucleotide). As would be recognized by one of skill in the art based on the present disclosure, methods of obtaining a bioelectronic signature and extracting various characteristics described herein can be used to determine the sequence of any biopolymer using any corresponding enzyme-of-interest, including but not limited to a polymerase, a nuclease, a proteasome, a glycopeptidase, a glycosidase, a kinase and an endonuclease. In some embodiments, the methods of the present disclosure include obtaining a bioelectronic signature of polymerase activity based on current fluctuations as each complementary nucleotidepolyphosphate monomer is incorporated into the template polynucleotide. In some embodiments, at least one characteristic of the bioelectronic signature identifies each of the complementary nucleotidepolyphosphate monomers incorporated into the template polynucleotide.

In accordance with these embodiments, the present disclosure also provides bioelectronic devices and systems in which the charge on a protein-of-interest is altered in order to modulate the overall conductance of a protein complex (e.g., a protein-of-interest and corresponding linker). For example, the conductance of a given protein complex in a bioelectronic device configured with platinum electrodes can be modulated (e.g., increased) to be similar to the conductance provided by gold electrodes by altering the charge of the protein complex (e.g., shifting the potential). Thus, embodiments of the present disclosure include a bioelectronic device that includes a first electrode and a second electrode separated by a gap, and a protein (e.g., a polymerase) attached to the first and second electrodes via a linker comprising a distinctive electrical charge. In some embodiments, the distinctive electrical charge modulates conductance through the protein in a manner that enhances the function of the bioelectronic device (e.g., sequencing of a biopolymer).

In some embodiments, the linker used to generate a bioelectronic device of the present disclosure includes a peptide or polypeptide. In some embodiments, the linker comprises streptavidin. In some embodiments, the linker comprises streptavidin that has been modified to have a positive or negative charge (e.g., with polyglutamate). In some embodiments, the protein-of-interest is biotinylated. In some embodiments, the linker comprises a distinctive negative charge. In some embodiments, the distinctive negative charge is conferred by addition of a glutamate moiety, an aspartate moiety, or a combination thereof (including derivatives, variants, and polymers), coupled to the streptavidin. In some embodiments, the distinctive negative charge increases the conductance through the protein. In some embodiments, the linker comprises a distinctive positive charge. In some embodiments, the distinctive positive charge is conferred by addition of an arginine moiety, a histidine moiety, a lysine moiety, or a combination thereof (including derivatives, variants, and polymers), coupled to the streptavidin. In some embodiments, the distinctive positive charge increases or decreases the conductance through the protein.

In accordance with the above embodiments, a polymerase can be functionally coupled to a first and second electrodes using a linker comprising streptavidin. In some embodiments, the polymerase is biotinylated. In some embodiments, the linker is attached to a region of the polymerase that is inactive. In some embodiments, the polymerase and the first and second electrodes are biotinylated, and the linker comprises a streptavidin molecule comprising at least two biotin binding sites. In some embodiments, the exonuclease activity of the polymerase is disabled. In some embodiments, the gap has a width of about 1.0 nm to about 20.0 nm. In some embodiments, the first and second electrodes are separated by a dielectric layer. In some embodiments, the method comprises applying a voltage bias between the first and second electrodes that is 100 mV or less.

Embodiments of the present disclosure also include a system for direct electrical measurement of polymerase activity. In accordance with these embodiments, the system includes any of the bioelectronic devices described herein, a means for introducing dNTPs capable of interacting with the polymerase, a means for applying a voltage bias between the first and second electrodes that is 100 mV or less, and a means for monitoring fluctuations that occur as the dNTPs are incorporated into a template polynucleotide by the polymerase.

As persons of ordinary skill in the art will readily recognize and appreciate after having benefited from the teachings of the present disclosure, the methods described herein can be used with any bioelectronic device that senses the duration of the open and closed states of an enzyme (e.g., polymerase). Exemplary devices include, but are not limited to, the bioelectronic devices and systems disclosed in U.S. Pat. No. 10,422,787 and PCT Appln. No. PCT/US2019/032707, both of which are herein incorporated by reference in their entirety and for all purposes.

4. Materials and Methods

Expression and Purification of Defined Valent Streptavidin Tetramers. Expression plasmids for hexaglutamate tagged Streptavidin (SAe) and Dead Streptavidin (D) were purchased through Addgene (plasmid #46367 & plasmid #20859). Plasmids were transformed into BL21 (DE3) pLysS for bacterial expression. Both expression and inclusion body purification were carried out following the detailed protocol from Howarth and Ting. Briefly, each variant was grown in 1 L of LB medium at 37° C. until an A600 of 0.8 was reached. Cultures were induced with 100 µg/mL isopropyl-β-D-thiogalactopyranoside at 37° C. for 4 hrs. Cells were harvested via centrifugation and lysed through the use of a mixture of B-PER (Pierce), lysozyme (10 mg/mL), and DNaseI (10 µg/mL). Inclusion bodies were pelleted and washed thoroughly with inclusion wash buffer (100 mM NaCl, 50 mM Tris pH 8.0, 0.5% Triton X-100) before resuspension in 6 M guanidinium hydrochloride (pH 1.5). Concentrations of solubilized SAe and D streptavidin were estimated via $A_{280}$ and combined in a 1:1 ratio. A mixed resuspension of SAe/D streptavidin was rapidly refolded in 250 mL of PBS dropwise from a 50 mL Burette with a controlled flow rate of ~1 drop/min. Following overnight stirring, the refolded protein was salted out using ammonium sulfate to remove unfolded proteins, contaminants, and to concentrate the refolded product. Purification of refolded SAe/D tetramers was first carried out via an initial 5 mL iminobiotin-sepharose gravity column. Proteins were loaded onto the resin using a 50 mM sodium borate, 300 mM NaCl, pH11.0 binding buffer, followed by elution with 20 mM $KH_2PO_4$, pH 2.2 buffer. Separation of the different SAe/D tetramer populations was accomplished using a 5 mL HiTrap Q column (GE) with 20 mM Tris buffers and salt gradient of 0.1M-0.5 M. All purification steps were adapted from Fairhead et al., Journal of Molecular Biology, Volume 426, Issue 1, 9 Jan. 2014, Pages 199-214.

Production of Biotinylated Φ29 Polymerase. The open reading frame of Φ29 Polymerase was cloned into the pET-15b expression vector for bacterial expression. Site specific biotinylation was achieved via addition of Avi-Tag in the N-terminus, just after a 6×His-tag, and incorporation of p-azido-L-phenylalanine (pAZF) through an amber stop codon. A Φ29 polymerase containing an amber codon at position W274 was used for the incorporation of pAZF as outlined by Chin et al. Briefly, the W274 amber codon Φ29 in pET-15b was co-transformed with the pEVOL-pAzF plasmid (Addgene plasmid #31186) into BL21 (DE3) competent cells and expressed. Purification of the expressed Φ29 Polymerase was accomplished via a 5 mL HisTrap column (GE), followed by secondary purification with a 5 mL HiTrap SP column (GE). The first biotinylation event was carried out through copper-free click reaction between pAZF in the mutant Φ29 Polymerase and biotin-PEG4-DBCO (Click Chemistry Tools). Singly biotinylated Φ29 Polymerase was separated from non-biotinylated protein using a monomeric avidin agarose resin (Pierce). Next, biotinylated Φ29 Polymerase was dually biotinylated using commercially available BirA ligase (Avidity) that specifically biotinylated the Avi-Tag. Biotinylation efficiency was checked following streptavidin reaction via molecular weight shift on SDS-PAGE.

Figure 8:
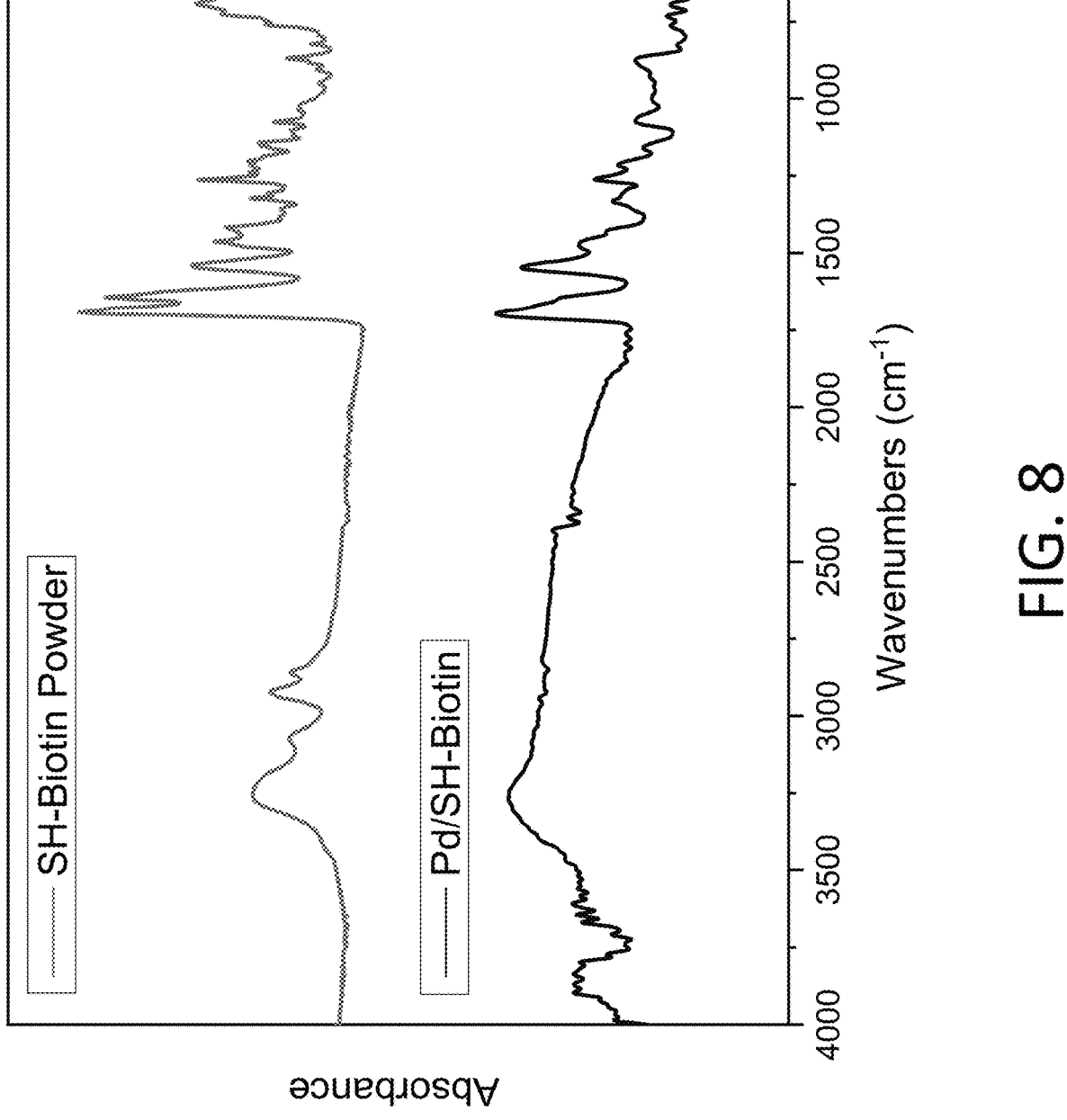
FIG. 8: FTIR characterization of Pd Chip functionalized with thiolated biotin. The red recording is the powder of disulfide biotin.

STM Conductance Measurements. Approximately 200 nm of Pd were deposited onto a 10 nm Cr adhesion layer on four inch p-type Si wafers using an e-beam evaporator (Lesker PVD 75), and functionalized as previously described. High density polyethylene-coated Pd probes were prepared as described previously. Conductance measurements were made in 1 mM phosphate buffer, pH 7.4, using a PicoSPM (Agilent) following the procedure described elsewhere. Samples and solutions were prepared as described earlier for biotin-streptavidin[1] and the biotin-streptavidin-polymerase Φ29 system, using a doubly-biotinylated engineered polymerase. The preparation of all solutions, and characterization of substrate surfaces is also described in these earlier publications. FTIR spectra taken from functionalized Pd substrates are given in FIG. 8.

For the electrochemical measurements, a salt-bridged reference electrode was constructed as described previously using 3M KCl for the rest potential measurements (210 mV on the NHE scale) and 10 mM KCl for the conductance measurements (360 mV on the NHE scale). Rest potentials were measured with a Fluke 177 meter (input impedance $>10^7 \Omega$) and potentials were stable to within ±5 mV over a period of hours. Sample to sample variation was ±5%.

What is claimed is:

1. A bioelectronic device comprising:
a first electrode;
a second electrode separated from the first electrode by a gap;
a protein; and
a linker comprising:
an assembly of monomers comprising a first ligand-binding monomer configured to bind to one or more ligands and a first non-ligand-binding monomer configured to not bind to the one or more ligands, and a tag comprising a first glutamate moiety or a first aspartate moiety or both; wherein the protein is attached to the first electrode and to the second electrode via the linker.

2. The bioelectronic device of claim 1, further comprising a second ligand-binding monomer.

3. The bioelectronic device of claim 1, further comprising a second non-ligand-binding monomer and a third non-ligand binding monomer.

4. The bioelectronic device of claim 1, further comprising a second non-ligand-binding monomer.

5. The bioelectronic device of claim 1, wherein the assembly of monomer comprises a first side and a second side opposite a first side and the first ligand-binding monomer is disposed on the first side, the bioelectronic device further comprising a second ligand-binding monomer disposed the second side.

6. The bioelectronic device of claim 1, wherein the assembly of monomer comprises a first side, the bioelectric device further comprising a second ligand-binding monomer disposed on a first side of the assembly of monomers and the first ligand-binding monomer is disposed the same first side.

7. The bioelectronic device of claim 1, wherein the linker further comprises a peptide or a polypeptide.

8. The bioelectronic device of claim 7, wherein the linker further comprises streptavidin.

9. The bioelectronic device of claim 1, wherein the tag further comprises a second glutamate moiety.

10. The bioelectronic device of claim 1, wherein the tag further comprises a hexaglutamate moiety.

11. The bioelectronic device of claim 1, wherein the first ligand-binding monomer includes a C-terminal end and the tag is coupled to a C-terminal end.

12. The bioelectronic device of claim 1, wherein the one or more ligands includes biotin.

13. The bioelectronic device of claim 1, wherein the protein comprises biotin covalently attached to the protein.

14. The bioelectronic device of claim 1, wherein the first electrode or the second electrode or both comprises gold, palladium, platinum, silver, copper, or a combination thereof.

15. The bioelectronic device of claim 1, wherein the protein is selected from the group consisting of a polymerase, a nuclease, a proteasome, a glycopeptidase, a glycosidase, a kinase, and an endonuclease.

16. The bioelectronic device of claim 1, wherein the protein includes an inactive region to which the linker is attached.

* * * * *